United States Patent
Vinluan et al.

(10) Patent No.: US 12,004,980 B2
(45) Date of Patent: *Jun. 11, 2024

(54) ADVANCED ENDOVASCULAR GRAFT AND DELIVERY SYSTEM

(71) Applicant: TriVascular, Inc., Santa Rosa, CA (US)

(72) Inventors: Jenine S. Vinluan, Petaluma, CA (US); William P. Stephens, Santa Rosa, CA (US); Mark Geusen, Santa Rosa, CA (US); Carl H. Poppe, Danville, CA (US); Christopher L Staudenmayer, Santa Rosa, CA (US); Michael V. Chobotov, Santa Rosa, CA (US); James R. Watson, Santa Rosa, CA (US); Teresa Woodson, Windsor, CA (US)

(73) Assignee: TriVascular, Inc., Santa Rosa, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/066,314

(22) Filed: Oct. 8, 2020

(65) Prior Publication Data

US 2021/0022895 A1     Jan. 28, 2021

Related U.S. Application Data

(60) Continuation of application No. 14/631,818, filed on Feb. 25, 2015, now Pat. No. 10,799,377, which is a
(Continued)

(51) Int. Cl.
*A61F 2/95*     (2013.01)
*A61F 2/07*     (2013.01)
(Continued)

(52) U.S. Cl.
CPC .................. *A61F 2/95* (2013.01); *A61F 2/07* (2013.01); *A61F 2/958* (2013.01);
(Continued)

(58) Field of Classification Search
CPC .... A61F 2/07; A61F 2/958; A61F 2002/9505; A61F 2002/9583; A61F 2/95; A61F 2/9661; A61F 2002/9665
See application file for complete search history.

(56) References Cited

U.S. PATENT DOCUMENTS 5,047,045 A     9/1991     Arney et al.
5,443,477 A     8/1995     Marin et al.
(Continued)

FOREIGN PATENT DOCUMENTS

EP     0621016     10/1994
EP     1 683 541 A2     7/2006
(Continued)

OTHER PUBLICATIONS

Extended European Search Report dated Jan. 27, 2015 in European Application No. EP 11841183.4 filed: Nov. 15, 2011.
(Continued)

*Primary Examiner* — Sarah W Aleman
(74) *Attorney, Agent, or Firm* — Foley & Lardner LLP

(57) ABSTRACT

Embodiments are directed in part to endovascular prostheses and methods of deploying same. Embodiments may be directed more specifically to stent grafts and methods of positioning and deploying such devices within the body of a patient.

20 Claims, 26 Drawing Sheets

Related U.S. Application Data division of application No. 13/297,219, filed on Nov. 15, 2011, now abandoned.

(60) Provisional application No. 61/414,375, filed on Nov. 16, 2010.

(51) Int. Cl.
| | |
|---|---|
| *A61F 2/958* | (2013.01) |
| *A61F 2/24* | (2006.01) |
| *A61F 2/848* | (2013.01) |
| *A61F 2/89* | (2013.01) |
| *A61F 2/915* | (2013.01) |
| *A61L 31/02* | (2006.01) |

(52) U.S. Cl.
CPC ... A61F 2002/072 (2013.01); A61F 2002/075 (2013.01); A61F 2/243 (2013.01); A61F 2/848 (2013.01); A61F 2002/8483 (2013.01); A61F 2/89 (2013.01); A61F 2002/91591 (2013.01); A61F 2002/9505 (2013.01); A61F 2002/9511 (2013.01); A61F 2210/0014 (2013.01); A61F 2210/0076 (2013.01); A61F 2220/0016 (2013.01); A61F 2220/005 (2013.01); A61F 2220/0058 (2013.01); A61F 2230/005 (2013.01); A61F 2230/0054 (2013.01); A61F 2250/0003 (2013.01); A61F 2250/0098 (2013.01); A61L 31/022 (2013.01)

(56) References Cited

U.S. PATENT DOCUMENTS

| | | | |
|---|---|---|---|
| 5,534,007 | A | 7/1996 | St. Germain et al. |
| 5,571,087 | A | 11/1996 | Ressemann et al. |
| 5,605,543 | A | 2/1997 | Swanson |
| 5,662,703 | A | 9/1997 | Yurek et al. |
| 5,683,452 | A | 11/1997 | Barone et al. |
| 6,395,018 | B1 | 5/2002 | Castaneda |
| 6,463,317 | B1 | 10/2002 | Kucharczky et al. |
| 6,582,460 | B1 | 6/2003 | Cryer |
| 6,641,606 | B2 | 11/2003 | Ouriel |
| 6,689,142 | B1 | 2/2004 | Tremaglio, Jr. |
| 7,014,653 | B2 | 3/2006 | Ouriel |
| 7,243,408 | B2 | 7/2007 | Vietmeier |
| 7,255,711 | B2 | 8/2007 | Holman et al. |
| 7,476,245 | B2 | 1/2009 | Abbate |
| 7,722,663 | B1 | 5/2010 | Austin |
| 7,998,189 | B2 | 8/2011 | Kolbel et al. |
| 8,066,755 | B2* | 11/2011 | Zacharias ............ A61F 2/91 623/1.36 |
| 8,206,427 | B1 | 6/2012 | Ryan et al. |
| 8,801,769 | B2 | 8/2014 | Chobotov |
| 9,364,314 | B2 | 6/2016 | Berra et al. |
| 2001/0023369 | A1 | 9/2001 | Chobotov |
| 2001/0037142 | A1 | 11/2001 | Stelter et al. |
| 2001/0047150 | A1 | 11/2001 | Chobotov |
| 2001/0049509 | A1 | 12/2001 | Sekine et al. |
| 2002/0026217 | A1* | 2/2002 | Baker ............ A61B 17/12022 606/225 |
| 2002/0026227 | A1 | 2/2002 | Philips |
| 2002/0156521 | A1 | 10/2002 | Ryan et al. |
| 2002/0161377 | A1* | 10/2002 | Rabkin ............ A61B 17/221 623/1.11 |
| 2003/0023248 | A1* | 1/2003 | Parodi ............ A61B 17/0682 606/139 |
| 2003/0199967 | A1 | 10/2003 | Hartley et al. |
| 2004/0044358 | A1 | 3/2004 | Khosravi et al. |
| 2004/0064083 | A1 | 4/2004 | Becker |
| 2004/0098091 | A1 | 5/2004 | Erbel et al. |
| 2004/0167619 | A1 | 8/2004 | Case |
| 2005/0004660 | A1 | 1/2005 | Rosenbluth et al. |
| 2007/0078506 | A1 | 4/2007 | McCormick et al. |
| 2007/0172526 | A1 | 7/2007 | Galdonik |
| 2007/0233220 | A1 | 10/2007 | Greenan |
| 2008/0132989 | A1 | 6/2008 | Snow et al. |
| 2008/0208240 | A1 | 8/2008 | Paz |
| 2008/0255652 | A1 | 10/2008 | Thomas et al. |
| 2008/0264102 | A1 | 10/2008 | Berra |
| 2008/0312671 | A1 | 12/2008 | Riles et al. |
| 2009/0125098 | A1 | 5/2009 | Chuter |
| 2009/0264988 | A1* | 10/2009 | Mafi ............ A61F 2/95 623/1.13 |
| 2010/0286760 | A1 | 11/2010 | Beach et al. |
| 2011/0257673 | A1 | 10/2011 | Heraty |
| 2011/0295356 | A1 | 12/2011 | Abunassar |
| 2013/0261734 | A1 | 10/2013 | Young et al. |
| 2013/0268048 | A1 | 10/2013 | Watson et al. |
| 2013/0268056 | A1 | 10/2013 | Chobotov et al. |
| 2013/0268057 | A1 | 10/2013 | Vinluan et al. |
| 2013/0338753 | A1 | 12/2013 | Geusen |
| 2015/0073523 | A1 | 3/2015 | Chobotov |

FOREIGN PATENT DOCUMENTS

| | | |
|---|---|---|
| WO | WO 9717898 | 5/1997 |
| WO | WO 01/76509 | 10/2001 |
| WO | WO 04/019823 | 3/2004 |
| WO | WO 05/115275 | 12/2005 |
| WO | WO 09/132309 | 10/2009 |
| WO | WO 16/065208 | 4/2016 |
| WO | WO 16/191602 | 12/2016 |
| WO | WO 17/019913 | 2/2017 |

OTHER PUBLICATIONS

Supplemental European Search Report dated Feb. 13, 2015 in European Application No. EP 11841183.4 filed: Nov. 15, 2011.

Extended European Search Report dated Oct. 8, 2015 in European Application No. EP 13771941.5 filed: Apr. 1, 2013.

Extended European Search Report dated Nov. 9, 2015 in European Application No. EP 13772199.9 filed: Mar. 29, 2013.

Office Action dated Mar. 13, 2015 in U.S. Appl. No. 12/245,620, filed Oct. 3, 2008 and published as: US2009/0099649 on Apr. 16, 2009.

Office Action dated Mar. 26, 2015 in U.S. Appl. No. 13/024,255 dated Feb. 9, 2011 and published as: US2011/0218609 on: Sep. 8, 2011.

Office Action Response dated Aug. 26, 2015 in U.S. Appl. No. 13/024,255 dated Feb. 9, 2011 and published as: US2011/0218609 on: Sep. 8, 2011.

Office Action dated Aug. 26, 2015 in U.S. Appl. No. 13/835,491, filed Mar. 15, 2013 and published as: 2013/0268048 on : Oct. 10, 2013.

Final Office Action dated Feb. 2, 2018, from U.S. Appl. No. 14/631,818.

Final Office Action dated Nov. 13, 2018, from U.S. Appl. No. 14/631,818.

Final Office Action dated Sep. 30, 2019, from U.S. Appl. No. 14/631,818.

Non-final Office Action dated Jul. 13, 2017, from U.S. Appl. No. 14/631,818.

Non-Final Office Action dated Jun. 13, 2018, from U.S. Appl. No. 14/631,818.

Non-Final Office Action dated Mar. 18, 2019, from U.S. Appl. No. 14/631,818.

Notice of Allowance dated Jun. 12, 2020, from U.S. Appl. No. 14/631,818.

Office Action dated Apr. 22, 2016 in U.S. Appl. No. 14/615,337 filed: Feb. 5, 2015 and published as: 2015-0157479 on Jun. 11, 2015.

Office Action Response dated Feb. 29, 2016 in U.S. Appl. No. 14/615,337 filed: Feb. 5, 2015 and published as: 2015-0157479 on Jun. 11, 2015.

Office Action dated Sep. 28, 2015 in U.S. Appl. No. 14/615,337 filed: Feb. 5, 2015 and published as: 2015-0157479 on Jun. 11, 2015.

(56) References Cited

OTHER PUBLICATIONS

International Search Report and Written Opinion dated Feb. 2, 2016 in International Patent Application No. PCT/US2015/057016 filed: Oct. 22, 2015 and published as: WO/2016/065208 on: Apr. 28, 2016.
International Search Report and Written Opinion dated Sep. 12, 2016 in International Patent Application No. PCT/US2016/034427 filed: May 26, 2016.
International Search Report and Written Opinion dated Dec. 1, 2016 in International Patent Application No. PCT/US2016/044583 filed: Jul. 28, 2016 and published as: WO/2017/019913 on: Feb. 2, 2017.
Office Action dated Oct. 3, 2016 in U.S. Appl. No. 13/024,255, filed Feb. 9, 2011 and published as: 2011/0218609 on: Sep. 8, 2011.
Office Action Response dated Apr. 7, 2016 in U.S. Appl. No. 13/024,255, filed Feb. 9, 2011 and published as: 2011/0218609 on: Sep. 8, 2011.
Office Action Response dated Apr. 3, 2017 in U.S. Appl. No. 14/615,337 filed: Feb. 5, 2015 and published as: 2015-0157479 on Jun. 11, 2015.
Final Office Action dated Dec. 1, 2016 in U.S. Appl. No. 14/615,337 filed: Feb. 5, 2015 and published as: 2015-0157479 on Jun. 11, 2015.
Office Action Response dated Aug. 18, 2016 in U.S. Appl. No. 14/615,337 filed: Feb. 5, 2015 and published as: 2015-0157479 on Jun. 11, 2015.
Office Action dated Jul. 29, 2016 in U.S. Appl. No. 13/835,491, filed Mar. 15, 2013 and published as: 2013/0268048 on: Oct. 10, 2013.
Office Action Response dated Feb. 16, 2016 in U.S. Appl. No. 13/835,491, filed Mar. 15, 2013 and published as: 2013/0268048 on: Oct. 10, 2013.
Office Action dated Dec. 11, 2015 in U.S. Appl. No. 13/024,255 dated Feb. 9, 2011 and published as: US2011/0218609 on: Sep. 8, 2011.
Non-Final Office Action dated May 19, 2017 in U.S. Appl. No. 14/615,337 filed: Feb. 5, 2015 and published as: 2015-0157479 on Jun. 11, 2015.
Request for Continued Examination dated Apr. 3, 2017 in U.S. Appl. No. 14/615,337 filed: Feb. 5, 2015 and published as: 2015-0157479 on Jun. 11, 2015.

* cited by examiner

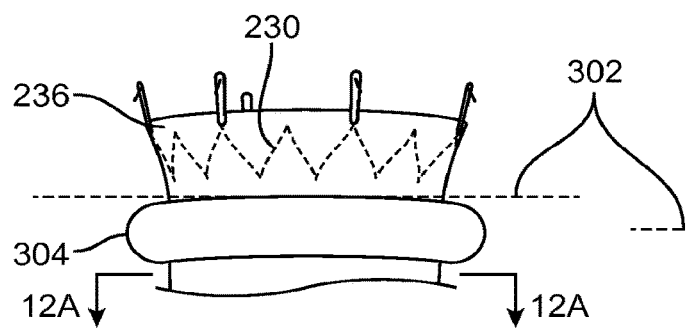
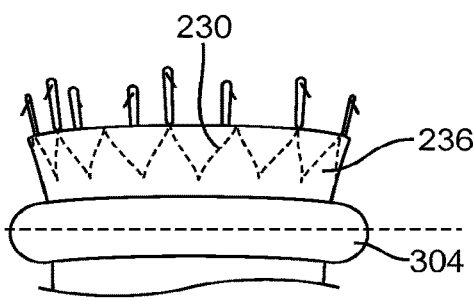
FIG. 12    FIG. 13
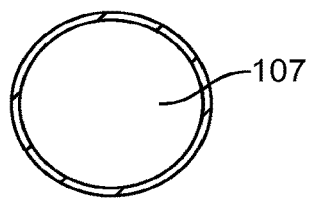
FIG. 12A
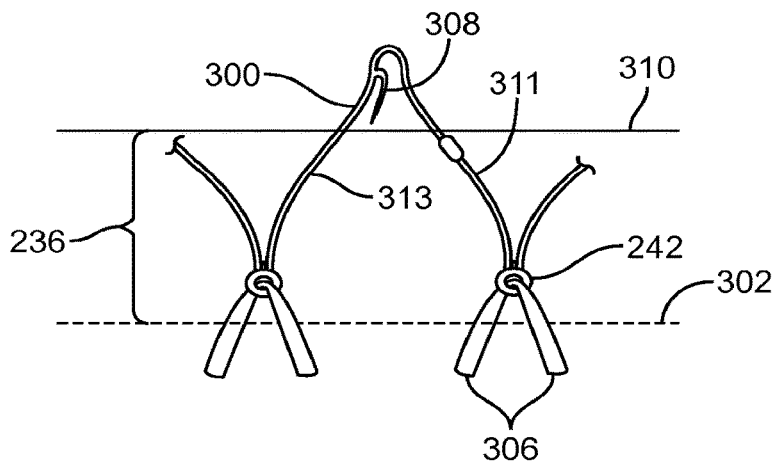
FIG. 14

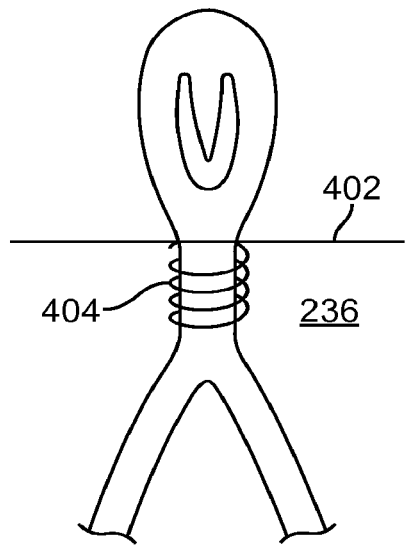 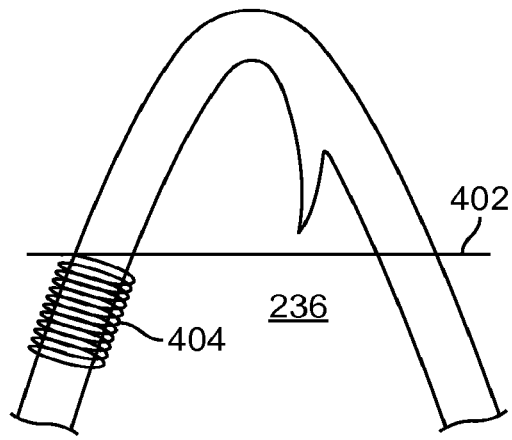
FIG. 15  FIG. 16
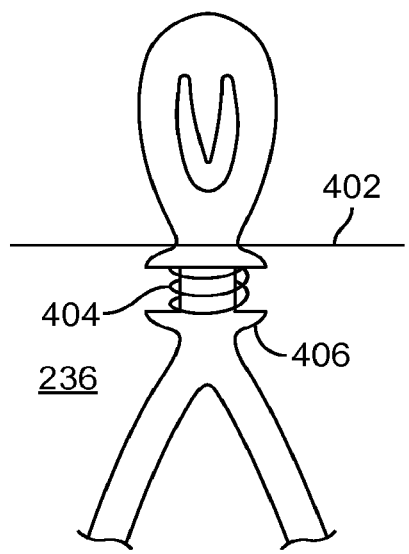 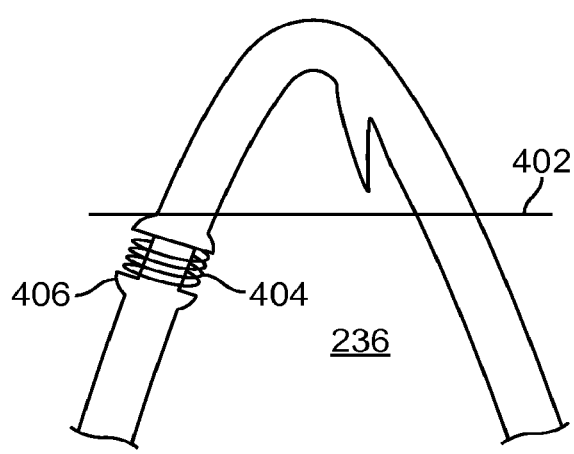
FIG. 17  FIG. 18

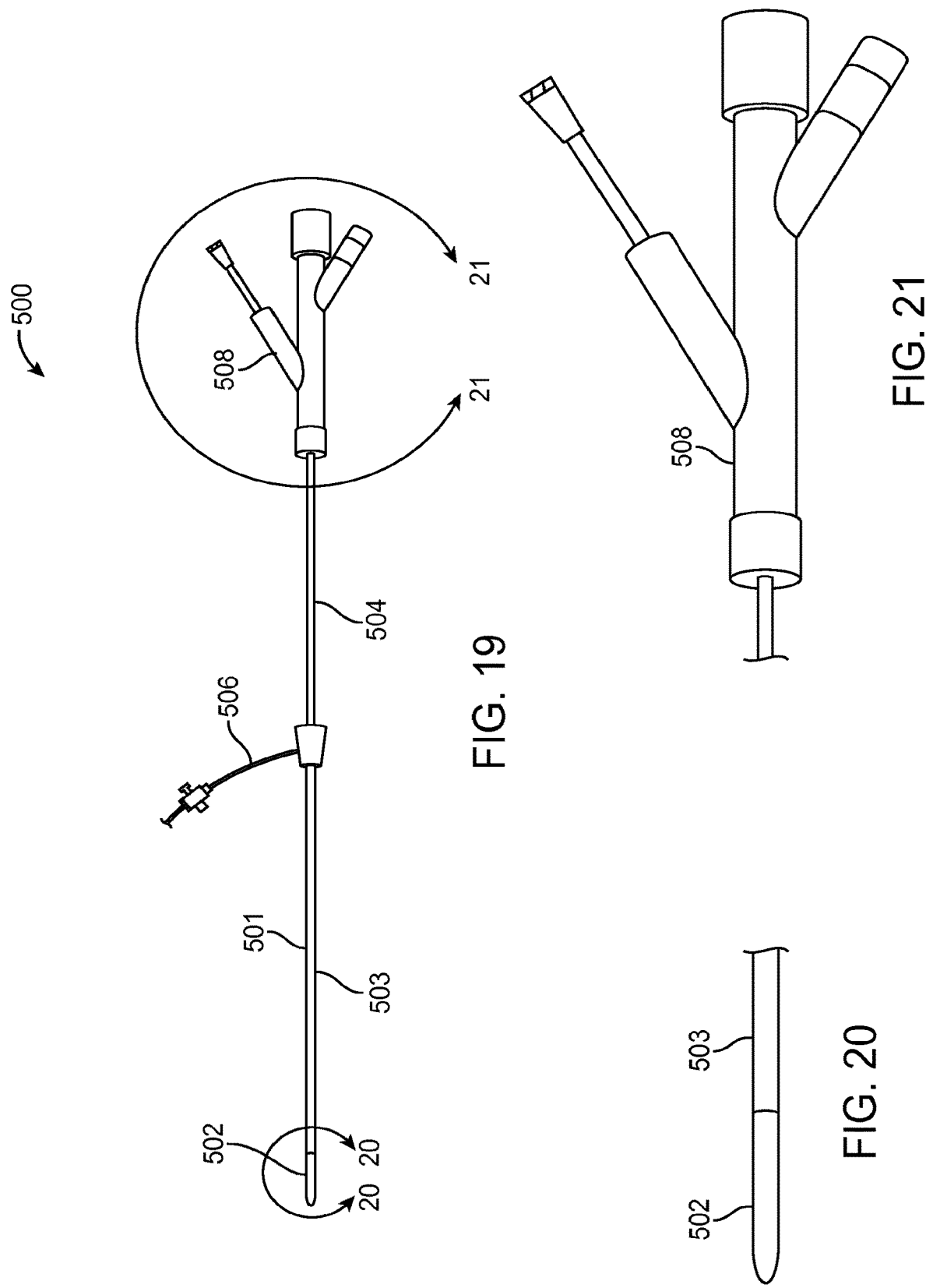

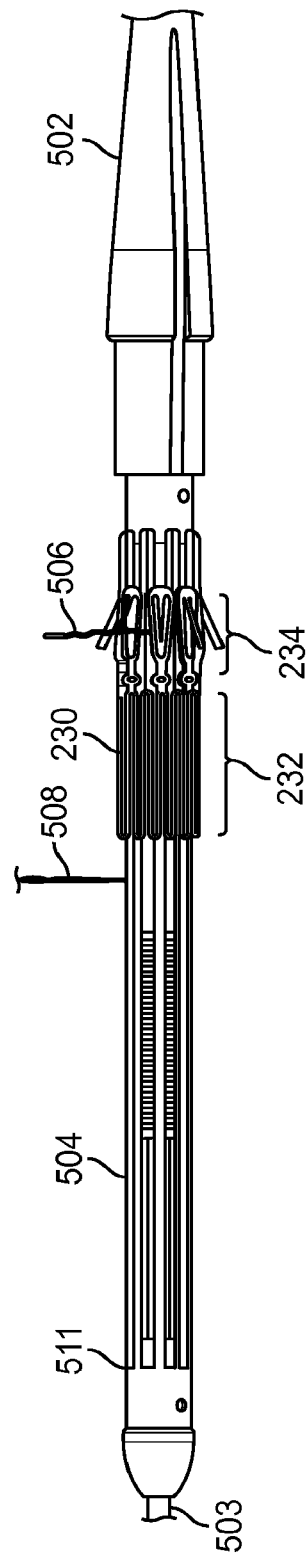
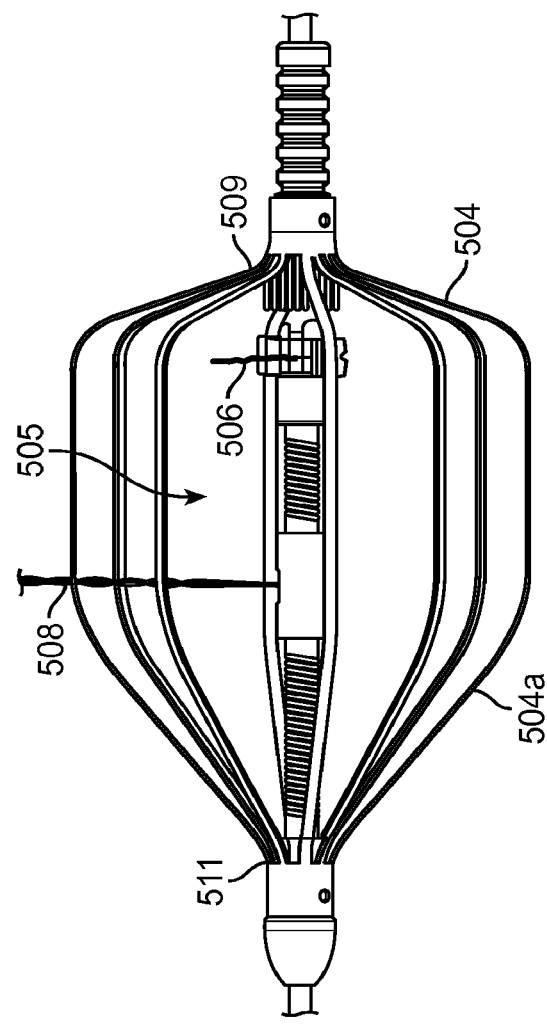
FIG. 22
FIG. 23

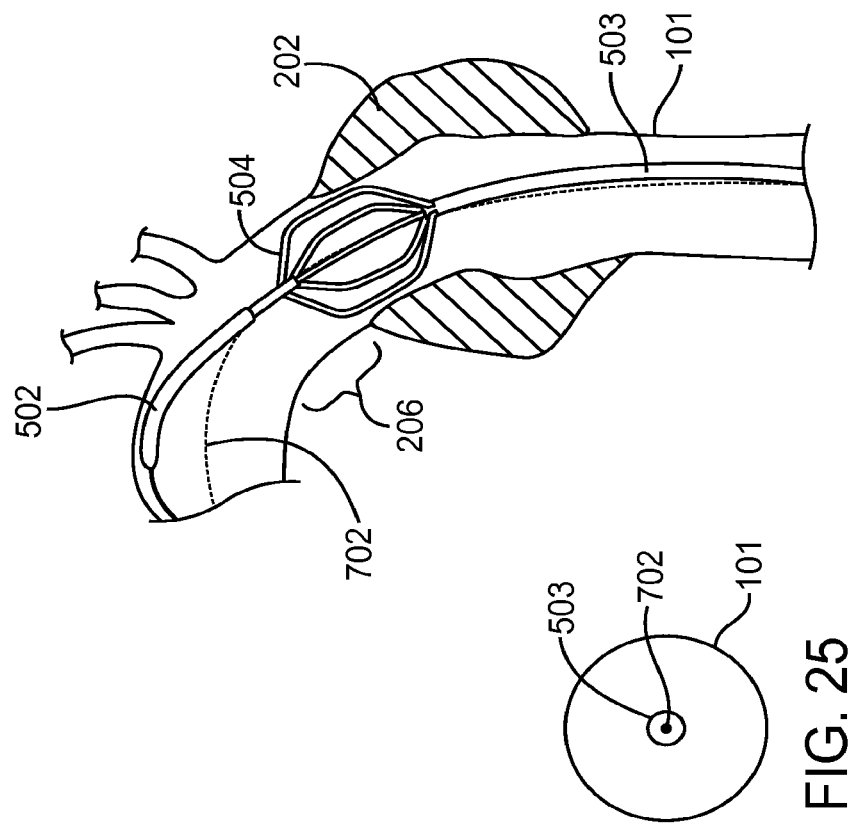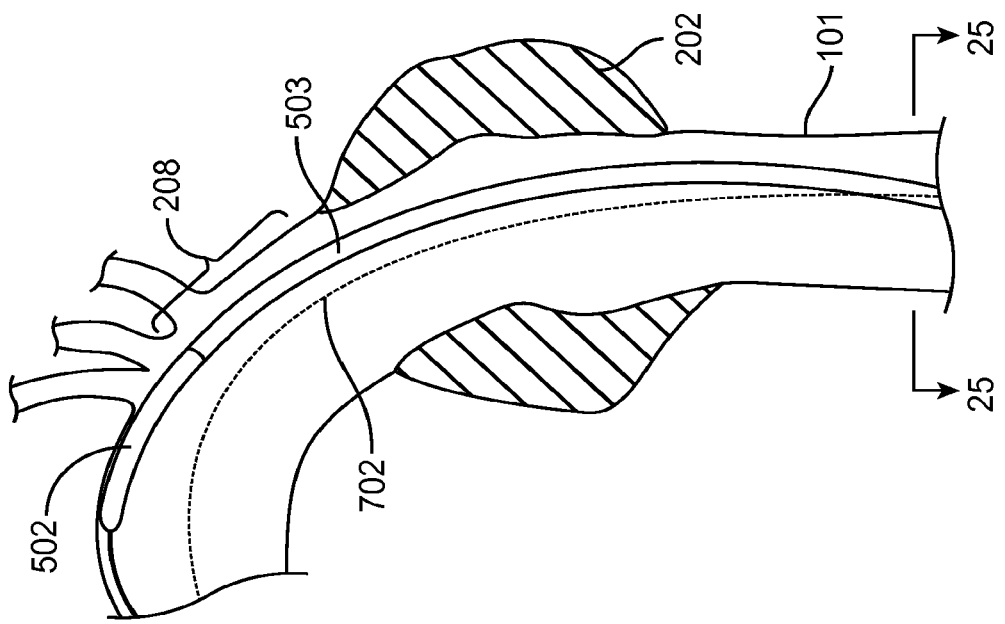

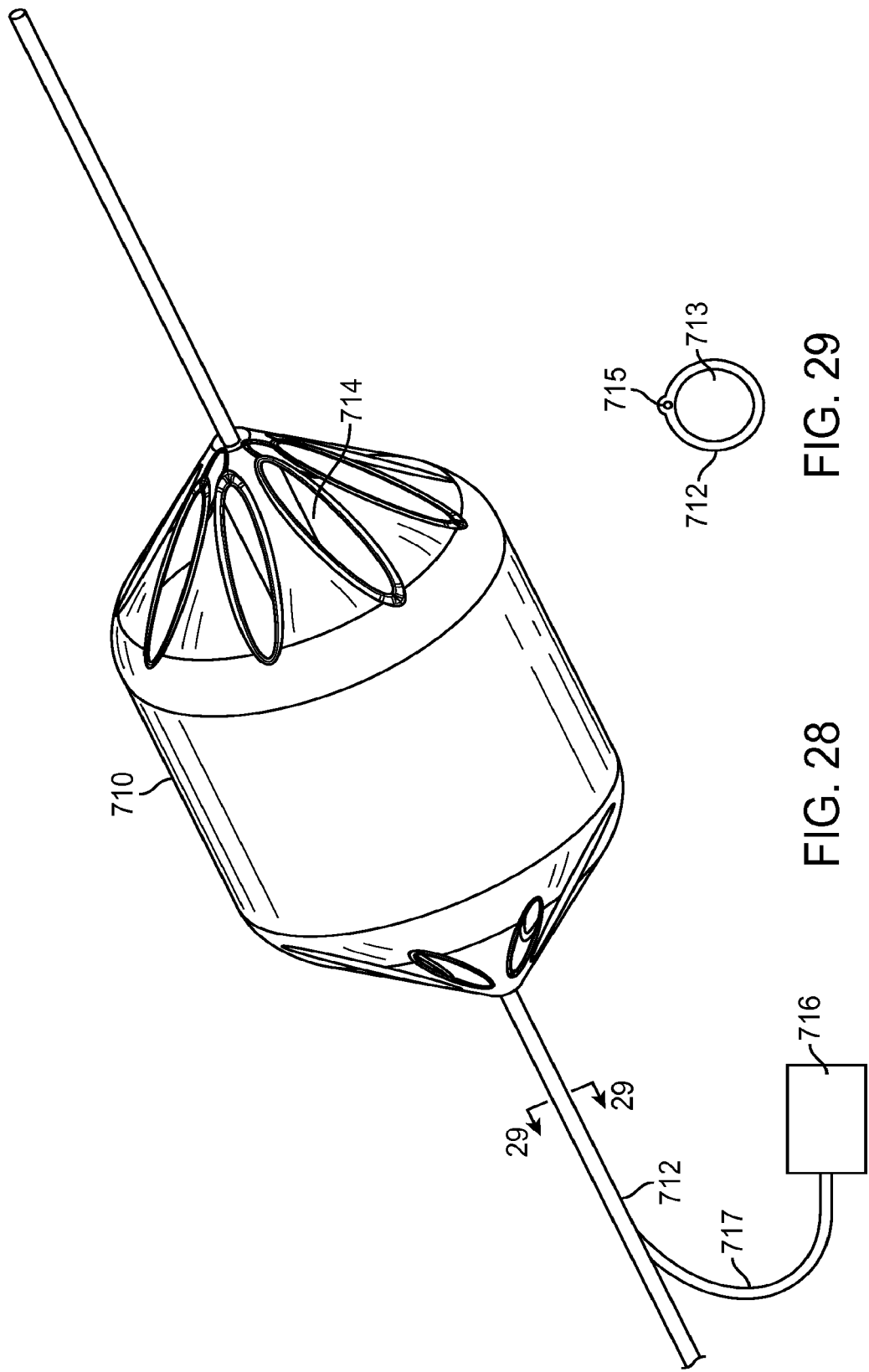

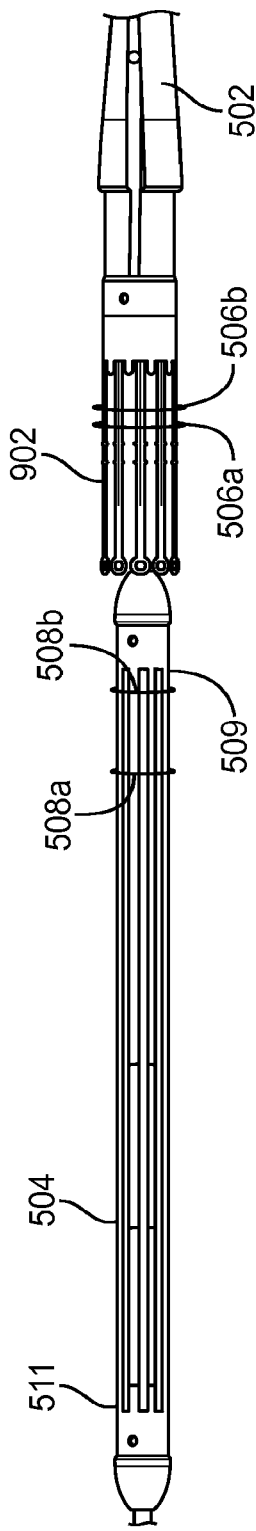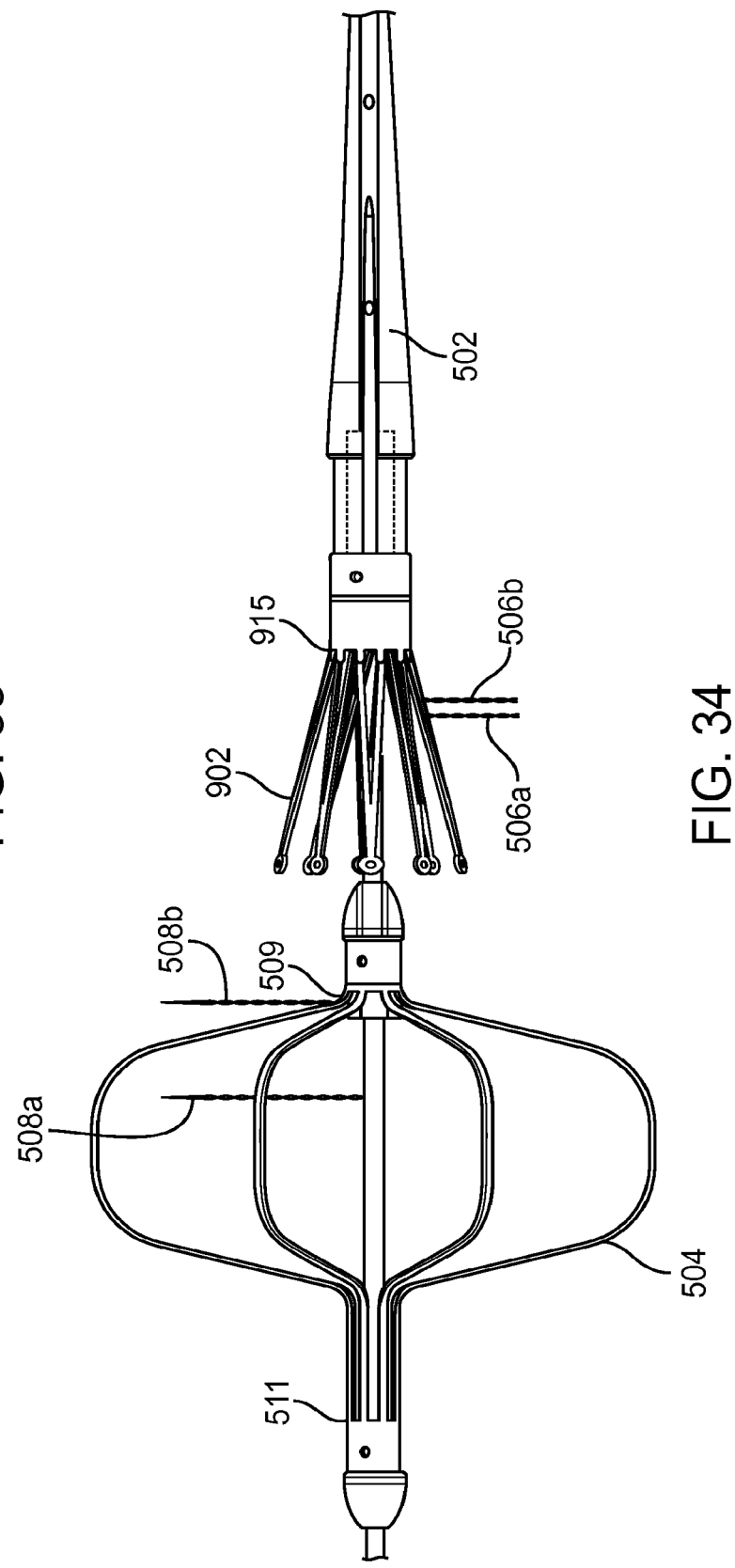

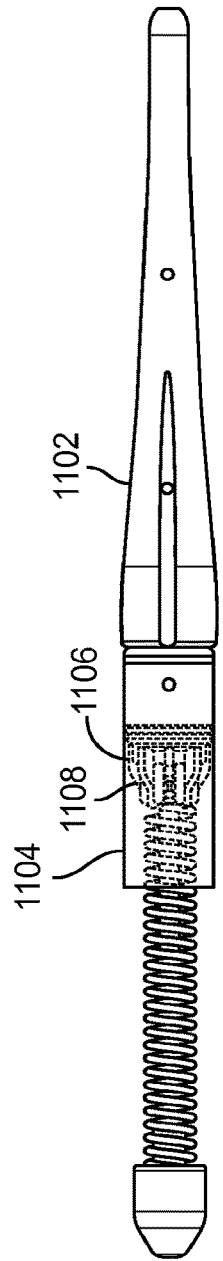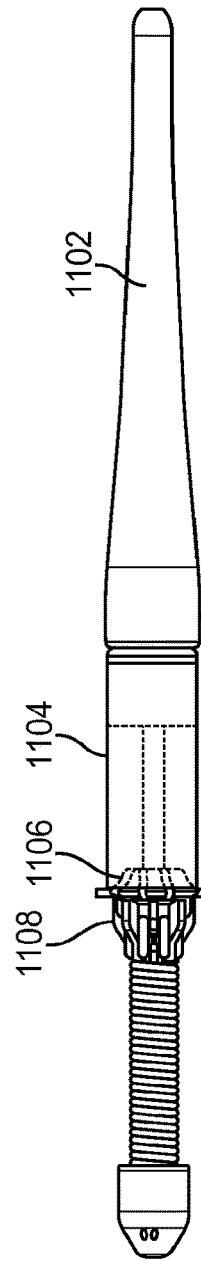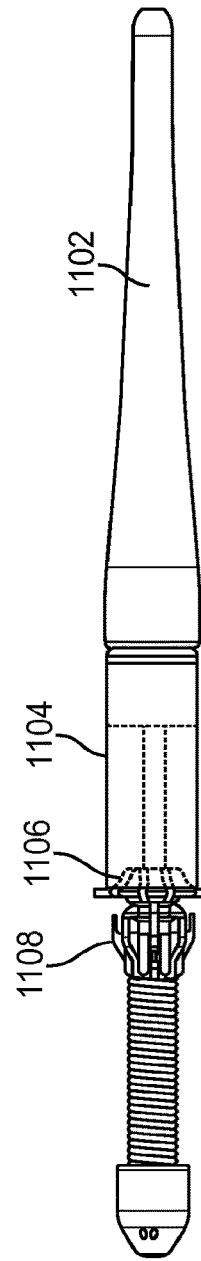

ADVANCED ENDOVASCULAR GRAFT AND DELIVERY SYSTEM

RELATED APPLICATIONS

This application is a continuation of U.S. patent application Ser. No. 14/631,818, filed Feb. 25, 2015, which is a divisional of U.S. patent application Ser. No. 13/297,219, filed Nov. 15, 2011, which claims priority under 35 U.S.C. section 119(e) from U.S. Provisional Patent Application Ser. No. 61/414,375, each of which are incorporated by reference herein in their entirety.

FIELD OF THE INVENTION

Some embodiments relate in part to endovascular prostheses and methods of deploying same. Embodiments may be directed more specifically to stent grafts and methods of making and deploying same within the body of a patient.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which may be a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of an AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989).

When deploying devices by catheter or other suitable instrument, it may be advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process.

In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated.

In addition to low profile, other features may be desirable as well. For example, it is well known that the AAA and TAA patient population presents a wide variety of anatomy for treatment. One particular challenge is providing stent-graft treatment to patients with either tortuous anatomies and/or small landing zones for stent-graft that have barbed stents to engage the luminal surface of the aorta or other vascular.

What have been needed are stent graft systems and methods that are adaptable to a wide range of patient anatomies and that can be safely and reliably deployed using a flexible low profile system.

SUMMARY

Some embodiments include advanced stent graft systems comprising, either singularly or in combination, a number of features. In some embodiments, a stent graft may include a short or no proximal stent portions. In other embodiments, proximal stent portions may include one or a plurality of barb structures. Other embodiments include various radiopaque marker embodiments.

Some embodiments may include advanced delivery systems having a centering device, such as a basket or an inflatable structure. Other embodiments show various constraints for loading of stent grafts within catheters. Other embodiments show various constraints in combination with centering devices.

Some embodiments of a stent graft may include a graft body including a flexible tubular main body having an inner lumen configured to confine a flow of fluid therethrough and a graft collar disposed at a proximal end of the main body. The stent graft may also include a stent having a distal stent portion which is disposed distally of a proximal edge of the graft collar. The distal stent portion may be at least partially secured to the graft collar. The stent may also have a proximal stent portion which is disposed proximally of the graft collar, includes at least one barb extending radially outward therefrom and includes an axial length of about 1 mm to about 5 mm.

Some embodiments of a method of deploying a stent graft in a patient's vessel include providing a stent graft having a graft body including a flexible tubular main body with an inner lumen configured to confine a flow of fluid therethrough and a graft collar disposed at a proximal end of the main body. The stent graft may also include a stent having a distal stent portion which is disposed distally of a proximal edge of the graft collar and which is at least partially secured to the graft collar. The stent may also have a proximal stent portion which is disposed proximally of the graft collar, includes at least one barb extending radially outward therefrom and includes an axial length of about 1 mm to about 5 mm. Thereafter, the stent graft may be axially positioned at a desired site within the patient's vessel with the at least one barb disposed axially coextensive with a viable landing zone of the patient's vessel. The stent may then be deployed so as to engage the tissue of the viable landing zone of an inner luminal wall of the patient's vessel.

Some embodiments of a delivery system for delivering a stent graft include a delivery catheter having an elongate shaft with a proximal section and a distal section. The system may also include a stent graft having a main graft body with an inner lumen configured for confining a flow of blood therethrough. The stent graft may be loaded on the proximal section of the delivery catheter with the elongate shaft disposed within the inner lumen. In addition, the delivery system may also include an expandable centering device disposed on the elongate shaft within the inner lumen of the stent graft. The centering device may be configured to expand from a radially contracted state to a radially expanded state for centering the elongate shaft and stent graft of the delivery system toward a midline or longitudinal axis of a patient's vessel when introduced into the patient's vessel. In some cases, the centering device includes an expanding basket, the basket having elongate tines that extend substantially parallel to the elongate shaft of the delivery catheter in the radially contracted configuration. The elongate tines may also be configured to bow radially outwardly from the elongate shaft in a substantially concentric arrangement in the radially expanded configuration. The centering device may also include an inflatable structure having a collapsed deflated state and an enlarged inflated state. In some cases, in the enlarged inflated state, the centering device may have a substantially cylindrical configuration including vias that extend from ports in a proximal surface of the centering device to respective ports in a distal surface of the centering device. The vias may be configured to provide for continuous flow of blood through the inflatable centering device and delivery system during inflation of the centering device and deployment of the stent graft.

Some embodiments of a method of centering a delivery system during deployment of a stent graft include providing a delivery system for delivering a stent graft. Such a delivery system may include a delivery catheter having an elongate shaft with a proximal section and a distal section. The delivery system may also include a stent graft having a main graft body with an inner lumen configured for confining a flow of blood therethrough and a stent secured to the main graft body, the stent graft being loaded on the proximal section of the delivery catheter with the elongate shaft disposed within the inner lumen. The delivery system may further include an expandable centering device disposed on the elongate shaft within the inner lumen. The centering device may be configured to expand from a radially contracted state to a radially expanded state for centering the elongate shaft and stent graft of the delivery system toward a midline longitudinal axis of a patient's vessel when introduced into the patient's vessel. Thereafter, the delivery catheter may be positioned within a patient's vessel such that the stent graft is axially positioned at a desired site within the patient's vessel. The expandable centering device may be in the radially contracted state during the positioning process in some cases. The expandable centering device may then be expanded to the radially expanded state to center the elongate shaft and stent graft of the delivery system toward the longitudinal axis of the patient's vessel. In addition, the stent of the stent graft may then be deployed so as to engage an inner luminal wall of the patient's vessel.

Some embodiments of a delivery system for delivering a stent graft include a delivery catheter having an elongate shaft with a proximal section and a distal section. The delivery catheter may also include a releasable stent constraint system disposed on the proximal section elongate shaft. In some cases, the stent constraint system may include a crown constraint sleeve having a rigid tubular structure disposed about the elongate shaft with a plurality of crown restraint extensions extending distally from the crown constraint sleeve. The crown restraint extensions may generally be circumferentially spaced from each other. The catheter may also have a strut support assembly which is slidingly disposed about the elongate shaft distally adjacent the crown constraint sleeve. The strut support assembly includes a plurality of strut supports which are circumferentially aligned with respective crown restraint extensions of the crown constraint sleeve and which extend radially away from a longitudinal axis of the elongate shaft. The constraint system has a docked state wherein the strut supports form closed but openable crown constraint passages between the strut supports and respective crown constraint extensions of the crown constraint sleeve. The constraint system also includes an open state wherein the strut support assembly is spaced axially away from the crown constraint sleeve and the crown restraint passages are opened to allow radial expansion of stent crowns disposed therein. The delivery system may also include a stent graft including a self-expanding stent secured to a proximal end of a main graft body. In some cases, the main graft body may have an inner lumen configured for confining a flow of blood therethrough. The stent graft is loaded on the proximal section of the delivery catheter with the elongate shaft disposed within the inner lumen and a plurality of proximal stent crowns disposed within closed crown restraint passages of the stent constraint system. So configured, the strut support assembly is in a docket state.

Some embodiments of a method of deploying a stent graft include providing a delivery system for delivering a stent graft. The delivery system may include a delivery catheter having an elongate shaft with a proximal section and a distal section and a releasable stent constraint system disposed on the proximal section elongate shaft. In some cases, the stent constraint system may include a crown constraint sleeve including a rigid tubular structure disposed about the elongate shaft with a plurality of crown restraint extensions extending distally from the crown constraint sleeve. Generally, the crown restraint extensions may be circumferentially spaced from each other. The stent constraint system may also include a strut support assembly which is disposed about the elongate shaft distally adjacent the crown constraint sleeve. The strut support assembly may include a plurality of strut supports which are circumferentially aligned with respective crown restraint extensions of the crown constraint sleeve and which extend radially away from a longitudinal axis of the elongate shaft. The constraint system is configured to have a docked state wherein the strut supports form closed but openable crown constraint passages between the strut supports and respective crown constraint extensions of the crown constraint sleeve. There is also an open state of the constraint system wherein the strut support assembly is spaced axially away from the crown constraint sleeve and the crown restraint passages are opened to allow radial expansion of stent crowns disposed therein. The delivery system further includes a stent graft having a self-expanding stent secured to a proximal end of a main graft body. The main graft body may have an inner lumen configured for confining a flow of blood therethrough. In some instances, the stent graft may be loaded on the proximal section of the elongate shaft with the elongate shaft disposed within the inner lumen and a plurality of proximal stent crowns disposed within closed crown restraint passages of the stent constraint system with the strut support assembly in a docket state. Such a stent graft may be axially positioning at a desired site within the patient's vessel. Thereafter, the crown restraint sleeve may be axially separated from the strut support assembly so as to open the crown restraint passages allowing crowns of the stent contained within the crown restraint passages to radially expand. In some instances, the crown constraint sleeve may be secured to elongate shaft and the strut support assembly may be slidingly disposed about elongate shaft distally adjacent the crown constraint sleeve. In such a case, axially separating the crown restraint sleeve from the strut support assembly so as to open the crown restraint passages allowing crowns of the stent contained within the crown restraint passages to radially expand may include displacing the strut support assembly in an axial direction relative to the crown constraint sleeve and the elongate shaft. In some cases, the strut support assembly is secured to the elongate shaft and the crown constraint sleeve is slidingly disposed about elongate shaft proximally adjacent the crown constraint sleeve. In such an embodiment, axially separating the crown restraint sleeve from the strut support assembly so as to open the crown restraint passages allowing crowns of the stent contained within the crown restraint passages may include displacing the crown constraint sleeve in a proximal direction relative to the strut support assembly and the elongate shaft.

Some embodiments of a delivery system for delivering a stent graft include a delivery catheter having an elongate shaft with a proximal section and a distal section. The delivery catheter may also include a releasable stent constraint system disposed on the proximal section elongate shaft. The stent constraint system may include a stent constraint sleeve which has a rigid tubular structure slidably disposed about the elongate shaft between a distal position and a proximal position. The stent constraint sleeve may also include a plurality of crown sections that extend distally from the crown constraint sleeve and are circumferentially spaced from each other. The constraint system may further include a plurality of strut supports which are secured to the elongate shaft distally adjacent the stent constraint sleeve, which are circumferentially spaced from each other and which extend radially away from a longitudinal axis of the elongate shaft. Such a constraint system may have a constraint state wherein the stent constraint sleeve is disposed in the distal position and a deployment state wherein the stent constraint sleeve is in the proximal position. The delivery catheter may also include an expandable basket having a plurality of elongate tines which are disposed in a substantially tubular configuration, which extend axially along the elongate shaft of the delivery catheter in a position distally adjacent the stent constraint sleeve, and which are configured to bow radially outward upon reduction of a separation between proximal ends of the elongate tines and distal ends of the elongate tines. In addition, the delivery system may have a stent graft including a flexible main graft body and a self-expanding stent. The main graft body portion may include an inner lumen configured for confining a flow of blood therethrough, a proximal end and a distal end. The self-expanding stent may have a proximal end, a distal end secured to the proximal end of the main graft body, and a plurality of proximal stent crowns which include at least one barb. For such a configuration, the stent graft may be loaded on the proximal section of the elongate shaft with the elongate shaft disposed within the inner lumen. The plurality of proximal stent crowns which include at least one barb may be disposed within and radially constrained by the stent constraint sleeve with the stent constraint sleeve in the distal position. In addition, at least one elongate tine of the expandable basket may be disposed beneath a stent crown that includes a barb, the at least one elongate tine being configured to apply outward radial force on the stent crown upon deployment of the stent and expansion of the expandable basket.

Some embodiments of a method of deploying a stent graft include providing a delivery system for delivering a stent graft. In some cases, such a delivery system may include a delivery catheter having an elongate shaft with a proximal section and a distal section. The delivery catheter may also include a releasable stent constraint system disposed on the proximal section elongate shaft. The stent constraint system may include a stent constraint sleeve which has a rigid tubular structure slidably disposed about the elongate shaft between a distal position and a proximal position. The stent constraint sleeve may also include a plurality of crown sections that extend distally from the crown constraint sleeve and are circumferentially spaced from each other. The constraint system may further include a plurality of strut supports which are secured to the elongate shaft distally adjacent the stent constraint sleeve, which are circumferentially spaced from each other and which extend radially away from a longitudinal axis of the elongate shaft. Such a constraint system may have a constraint state wherein the stent constraint sleeve is disposed in the distal position and a deployment state wherein the stent constraint sleeve is in the proximal position. The delivery catheter may also include an expandable basket having a plurality of elongate tines which are disposed in a substantially tubular configuration, which extend axially along the elongate shaft of the delivery catheter in a position distally adjacent the stent constraint sleeve, and which are configured to bow radially outward upon reduction of a separation between proximal ends of the elongate tines and distal ends of the elongate tines. In addition, the delivery system may have a stent graft including a flexible main graft body and a self-expanding stent. The main graft body portion may include an inner lumen configured for confining a flow of blood therethrough, a proximal end and a distal end. The self-expanding stent may have a proximal end, a distal end secured to the proximal end of the main graft body, and a plurality of proximal stent crowns which include at least one barb. For such a configuration, the stent graft may be loaded on the proximal section of the elongate shaft with the elongate shaft disposed within the inner lumen. The plurality of proximal stent crowns which include at least one barb may be disposed within and radially constrained by the stent constraint sleeve with the stent constraint sleeve in the distal position. In addition, at least one elongate tine of the expandable basket may be disposed beneath a stent crown that includes a barb, the at least one elongate tine being configured to apply outward radial force on the stent crown upon deployment of the stent and expansion of the expandable basket. For such a system the stent graft may be axially positioned at a desired site within the patient's vessel and the stent constraint sleeve axially displaced in a proximal direction from the distal position to the proximal position to release the crowns of the stent to radially expand. In addition, the expandable basket may be radially expanded such that at least one elongate tine of the expandable basket which is disposed beneath a corresponding crown having a barb extends radially outward and applies an outward radial force to the corresponding crown so as to facilitate engagement of the barb with tissue of the patient's vessel at the desired site.

Certain embodiments are described further in the following description, examples, claims and drawings.

BRIEF DESCRIPTION OF THE DRAWINGS

FIG. 12 shows an embodiment of stent structure formed onto a graft collar.

FIG. 12A is a transverse cross section view of the graft of FIG. 12 taken along lines 12A-12A of FIG. 12.

FIG. 13 shows an embodiment of stent structure formed onto a graft collar.

FIG. 14 shows an embodiment of stent structure formed onto a graft collar.

FIG. 15 shows an embodiment of a barb structure as positioned with respect to a graft collar or proximal edge thereof and an embodiment of a radiopaque marker.

FIG. 16 shows an embodiment of a barb structure as positioned with respect to a graft collar or proximal edge thereof and an embodiment of a radiopaque marker.

FIG. 17 shows an embodiment of a barb structure as positioned with respect to a graft collar or proximal edge thereof and an embodiment of a radiopaque marker.

FIG. 18 shows an embodiment of a barb structure as positioned with respect to a graft collar or proximal edge thereof and an embodiment of a radiopaque marker.

FIG. 19 shows an exemplary catheter delivery system embodiment.

FIG. 20 shows an enlarged view of the nosecone of the delivery catheter of FIG. 5.

FIG. 21 shows an enlarged view of a handle portion of the delivery catheter of FIG. 5.

FIG. 22 shows an embodiment of a delivery system including an expandable basket arrangement in a radially constrained state.

FIG. 23 shows the expandable basket arrangement of FIG. 22 in a radially expanded state with closer spacing between distal and proximal ends of the basket than in FIG. 22.

FIG. 24 depicts a delivery catheter being positioned inside a patient's aorta.

FIG. 25 shows a transverse cross section view of the delivery catheter within the patient's aorta of FIG. 24 taken along lines 25-25 of FIG. 24.

FIG. 26 shows the delivery catheter of FIG. 24 with a centering basket deployed.

FIG. 28 is a perspective view of an embodiment of a centering device including an inflatable structure.

FIG. 29 is a transverse cross section view of a dual lumen elongate tubular member that includes a lumen for a guidewire and an inflation lumen for the inflatable structure.

FIG. 33 shows an embodiment of a basket configuration of a delivery catheter with the basket and a stent of the stent graft loaded thereon in a radially constrained state.

FIG. 34 shows the delivery catheter and stent graft of FIG. 33 with the stent partially deployed and the basket in a radially expanded state.

FIG. 42 is an elevation view of the constraint system of FIG. 40 crown constraint assembly and support disposed in a proximal position configured to constrain a stent which is not shown for purposes of clarity of illustration.

FIG. 43 is an elevation view of the constraint system as shown in FIG. 42 but with the crown constraint assembly disposed distally of the proximal edge of the sleeve but still engaged with the support.

FIG. 44 shows the constraint system of FIG. 43 with the crown constraint assembly disposed distally of the sleeve and distally disengaged from the support so as to fully release a previously constrained stent.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DETAILED DESCRIPTION

Embodiments may be directed generally to methods and devices for treatment of fluid flow vessels with the body of a patient. Treatment of blood vessels is specifically indicated for some embodiments, and, more specifically, treatment of aneurysms, such as thoracic aortic aneurysms and abdominal aortic aneurysms. Prosthetic devices used for the treatment of fluid flow vessels within a patient's body are typically subjected to a variety of forces such as pulsatile expansion and contraction of a patient's vessels as well as significant hemodynamic forces resulting from a high rate of flow of blood through the vessels. Often diseased vessels that require treatment are tortuous and narrow making percutaneous delivery of the prosthetic to the treatment site difficult. As such, it may be important for a prosthetic such as a stent graft to be configured to securely anchor to an inner luminal surface of the patient's vessel to prevent axial slippage or movement of the device after deployment. Such anchoring may be necessarily carried out in a short axial section of relatively healthy vessel tissue in order to properly secure the device. As such, some stent graft embodiments may require a configuration that may be securely anchored within such constraints. It may also be important for the stent graft to establish a good seal between an outside surface of the stent graft and the inner luminal surface of the patient's vessel in order to effectively isolate the vascular defect such as an aneurysm from the hemodynamic forces of blood flow. Proper placement of the prosthetic at deployment may also be a challenge and thus some delivery system embodiments used to deploy a prosthetic for treatment of a patient's aneurysm may be configured to accurately position the stent graft as well as allow for partial deployment and repositioning of the stent graft prior to full deployment.

Figure 1:
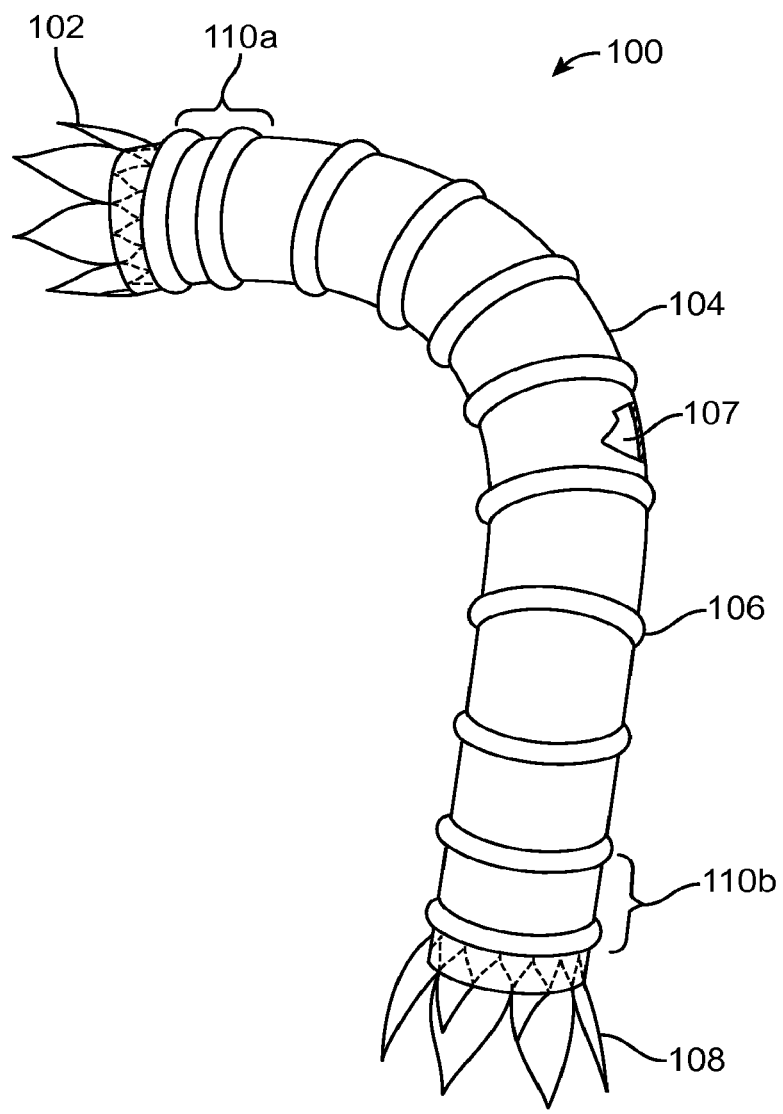
FIG. 1 is a perspective view of an embodiment of an inflatable stent graft.

FIG. 1 is a perspective view of an inflatable stent graft 100 made particularly for TAA. Such a stent graft 100 may have features which are similar to or the same as those of the Ovation™ Stent Graft System of TriVascular Inc. Stent graft 100 may include a proximal stent 102 having a substantially tubular overall configuration, a main graft body 104 also having a substantially tubular overall configuration, inflation channels 106 disposed on the flexible main graft body 104 and distal stent 108 having a substantially tubular configuration. Stents 102 and 108 may be made from any suitable material. For example, self-expanding stent embodiments 102 and 108 may be made from superelastic materials such as NiTi alloy or the like or any other suitable high strength material. Stent embodiments 102 and 108 that are configured to be balloon expandable may be made from other high strength materials such as stainless steel, MP35N, Elgiloy® or the like. Inflation sealing rings 110a and 110b may be included to provide a better sealing between an outside surface of the stent graft 100 and an inner luminal surface of the patient's vessel. Such an improved seal may be helpful in reducing or preventing the possibility of endoleaks that might occur around the fabric or layers of the main graft body 104 stent graft. The inflation sealing rings or expandable cuffs 110a and 110b may have an interior volume that is in fluid communication with an interior volume of the inflation channels 106.

Figure 5:
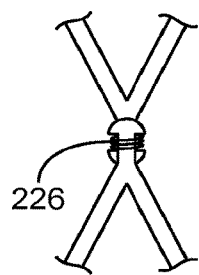
FIG. 5 shows an enlarged view of a connection between a proximal stent portion and distal stent portion.

The distal end of the proximal stent 102 is secured to a connection ring or sealing ring disposed within a proximal end of the main graft body 104. A proximal end of the distal stent 108 is secured to a connection ring or sealing ring disposed in a distal end of the main graft body 104. The stents 102 and 108 may be secured by any suitable method or device discussed or incorporated herein such as the "dogbone" type connection discussed below with regard to FIG. 5.

Main graft body 104 may be made from any suitable flexible biocompatible material for constructing such stent grafts. For example, body 104 might be made from a fabric such as Dacron®, from a polymer such as a fluoropolymer like polytetrafluorethylene (PFTE) or expanded PTFE (ePTFE) or any other suitable material. Ins some instances, it may be desirable for the material of the main graft body to be configured to be thin and flexible in order to pack tightly for a reduced profile during delivery and be configured to confine a flow of blood through a tubular structure made of the material. In cases, the type of material used for the main graft body and whether the main graft body includes inflation channels and inflation sealing rings may be of less importance. Some embodiments may, however, include a main graft body made of PTFE and have inflation channels and sealing rings. In some cases the main graft body 104 may have an axial length of about 50 mm to about 400 mm, more specifically, about 100 mm to about 300 mm. In some cases, an inner lumen 107 configured to confine a flow of blood or other bodily fluid therethrough of the main graft body 104 my have a transverse diameter or dimension of about 15 mm to about 39 mm, more specifically, about 30 mm to about 36 mm. The proximal and distal stents 102 and 108 may have dimensions commensurate with those of the main graft body 104. The stents 102 and 108 may have any suitable number of crowns or apices depending on the transverse expanded dimension or diameter and axial length of the stents 102 and 108. In some cases, the sinusoidal structure of the stents 102 and 104 may have about 3 to about 16 apices per side.

Embodiments having such construction which may be substituted into or included with any of the suitable embodiments discussed here are generally disclosed in commonly-owned U.S. Pat. No. 6,331,191, filed Nov. 25, 1998, by Chobotov, titled "Layered Endovascular Graft"; U.S. Pat. No. 6,395,019 filed Aug. 14, 1998, by Chobotov, titled "Endovascular Graft"; U.S. Pat. No. 6,602,280 filed Jan. 31, 2001, by Chobotov, titled "Delivery System and Method for Expandable Intracorporeal Device"; U.S. Pat. No. 6,733,521 filed Apr. 11, 2001, by Chobotov, et al., titled "Delivery System and Method for Endovascular Graft"; U.S. Pat. No. 6,761,733 filed Jul. 27, 2001, by Chobotov et al., titled "Delivery System and Method for Bifurcated Endovascular Graft"; U.S. Pat. No. 6,776,604 filed Dec. 20, 2001, by Chobotov et al., titled "Method and Apparatus for Shape Forming Endovascular Graft Material"; U.S. Pat. No. 7,066,951 filed Apr. 17, 2003, by Chobotov, titled "Delivery System and Method for Expandable Intracorporeal Device"; U.S. Pat. No. 7,081,129 filed Apr. 24, 2002, by Chobotov, titled "Endovascular Graft"; U.S. Pat. No. 7,147,660 filed Dec. 20, 2002, by Chobotov et al., titled "Advanced Endovascular Graft"; U.S. Pat. No. 7,147,661 filed Dec. 20, 2001, by Chobotov et al., titled "Radially Expandable Stent" and U.S. Pat. No. 7,150,758 filed Mar. 6, 2003, by Kari et al., titled "Kink Resistant Endovascular Graft"; and in United States Published Patent Application Numbers 2005/0027347, Aug. 13, 2003, by Chobotov et al., titled "Endovascular Graft Joint and Method for Manufacture"; 2006/0222596 filed Apr. 1, 2005, by Askari et al., titled "Non-Degradable, Low Swelling, Water Soluble Radiopaque Hydrogel Polymer"; 2006/0233990 filed Apr. 13, 2005, by Humphrey et al., titled "PTFE Layers and Methods of Manufacturing"; 2006/0233991 filed Apr. 13, 2005, by Humphrey et al., titled "PTFE Layers and Methods of Manufacturing"; 2009/0082845 filed Sep. 26, 2007, by Chobotov, titled "Alignment Stent Apparatus and Method"; 2009/0082846 filed Sep. 26, 2007, by Chobotov, titled "Asymmetric Stent Apparatus and Method" and 2009/0099649 filed Oct. 3, 2008, by Chotobov et al., titled "Modular Vascular Graft for Low Profile Percutaneous Delivery"—all such patents and patent applications are fully incorporated by reference in their entirety herein. In addition, any suitable stent graft, delivery system or components thereof disclosed in these incorporated patent and patent applications may be substituted for embodiments of same discussed herein.

Figure 2:
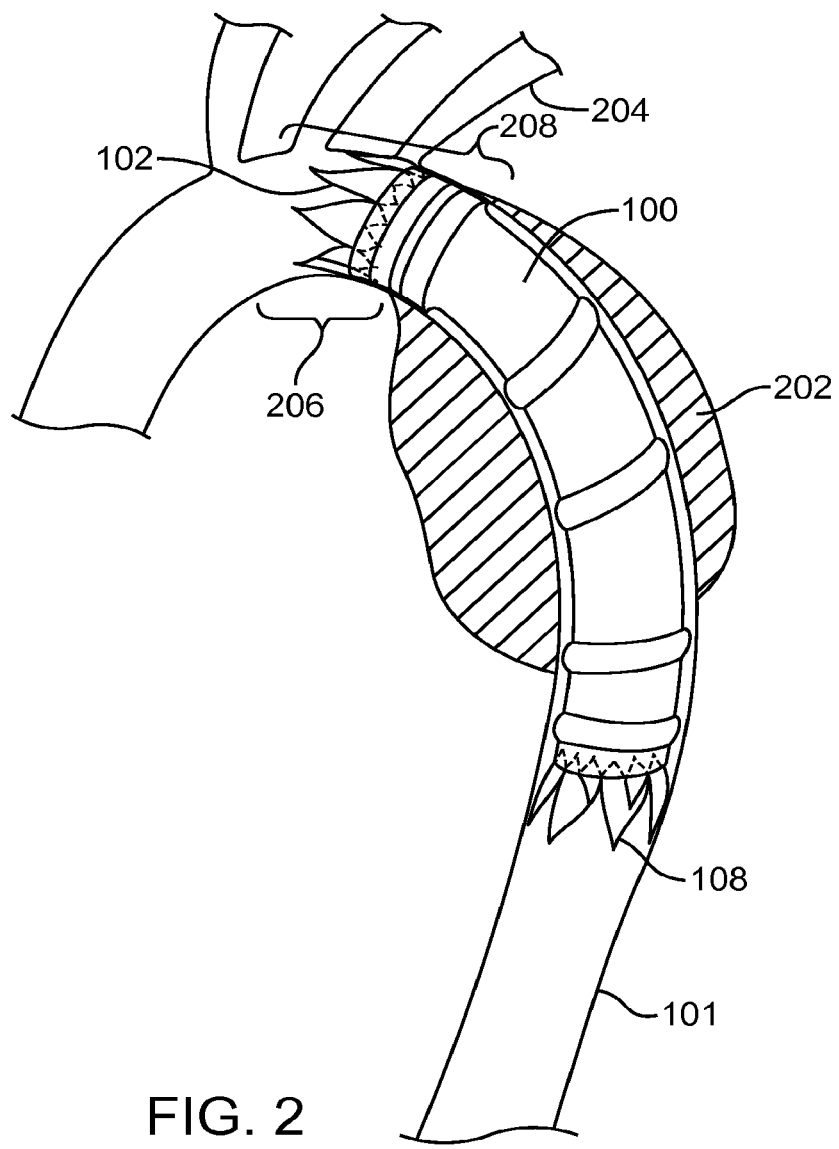
FIG. 2 shows the stent graft of FIG. 1 as placed in a vessel lumen of a patient having a TAA condition in partial section.

FIG. 2 shows an elevation view in partial section of the stent graft embodiment 100 of FIG. 1 as implanted and deployed in an aorta 101 of a patient having a TAA condition 202. As shown, stent graft 100 is implanted in such a manner so as to establish a good hemostatic seal between an outside surface of the stent graft 100 at the inflation seals 110a and the proximal stent deployed at a suitable landing zone so as not to occlude the left subclavian artery 204 with the fabric or other flexible layers of the stent graft 100. In this case, the aneurysm 202 has been effectively isolated from the nominal blood flow through the vessel 101. The nominal blood may flow pass through the inner lumen of the main graft body 104 and stents 102 and 108 after such deployment of the stent graft 100. In some cases, proximal stent 102 may be deployed proximally of the left subclavian artery 204 of the patient and optional barbs shown in FIG. 3 may be used to better fixate the stent grafts 102 and 108 by engaging with the luminal surface of the aorta 101. Stent graft 100 as well as others discussed herein may also be deployed such that the left subclavian artery 204 is covered by the fabric or layers of the main graft portion 104—up to the left common carotid artery with a trans-graft between the left subclavian and one of the adjoining arteries.

As mentioned above, patient anatomy may be widely varied—with some patients having extreme neck angulation and curvature of the aorta (as depicted in vessel element or section 206 and vessel element or section 208 of FIG. 2. Vessel section 206 may be described as being the lesser-curve side of the aorta and vessel section 208 may be described as the greater-curve section of the patient's aorta 101. Vessel section of the greater curve 208 may also have a short axial length section or "landing zone" for securing a proximal stent 102 of a stent graft 100. In some cases, such extreme conditions of short landing zones may rule out a particular patient for treatment by any known endograft because the risk of certain failure modes may be too great. Such failure modes might include stent breakage (because of extreme hemodynamic conditions in the thoracic aorta); insufficient sealing or the like. It will be appreciated that such extreme conditions of neck angulation and curvature and short landing zones may also appear in AAA conditions and, therefore, the devices and techniques of the present disclosure may also be desirable in the treatment of AAA conditions—or anywhere in a patient's body where such conditions may exist.

Figure 3:
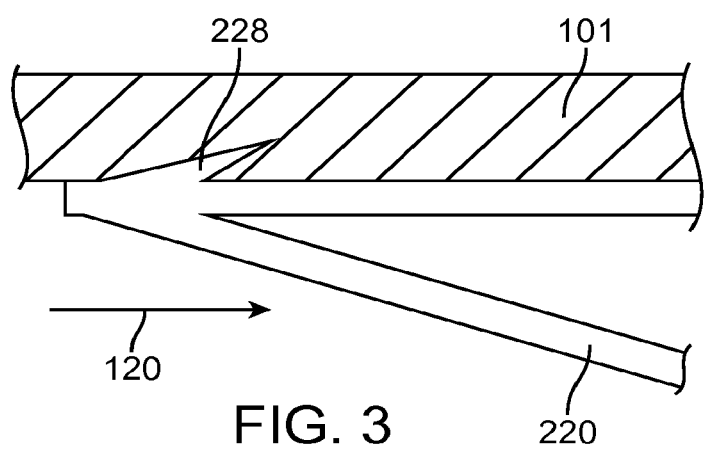
FIG. 3 shows an enlarged view in partial section of a barb of a proximal stent of the stent graft of FIG. 1 penetrating and engaged with tissue of the patient's vessel.

FIG. 3 is an elevation view in partial section of a proximal portion of a proximal stent 220 of a stent graft such as stent graft 100 discussed above. An optional barb 228 of the stent 220 is extending from a strut of the stent 220 at an angle pointing substantially in a distal direction along a direction of a flow of blood in the vessel 101 of the deployment. The barb 228 is also angled slightly radially outward towards the vessel wall 101 in order to penetrate and mechanically engage the tissue of the patient's vessel 101. Such a barb arrangement may be incorporated in to any suitable stent embodiment discussed herein. In addition, although FIG. 3 depicts the engagement of a proximal stent with a patient's vessel 101, a similar arrangement and deployment configuration may be used for distal stents, such as distal stent 108 and the like but with the directions of the stent and barb 228 reversed relative to the direction of blood flow as indicated by arrow 120.

Several embodiments of stents that might serve as either proximal stents or distal (if any) stents on a stent graft are discussed herein. If a stent graft is destined to be placed into an area of challenging anatomy, short landing zones or in an area where the hemodynamics are challenging (e.g. high pressure and blood velocity, such as found near the heart in the thoracic aorta), then it may be desirable to have a stent that is not susceptible to failure (e.g. stent fractures) or to damaging the patient's vasculature (in the case of movement of the stent in vivo due to blood flow).

Figure 4:
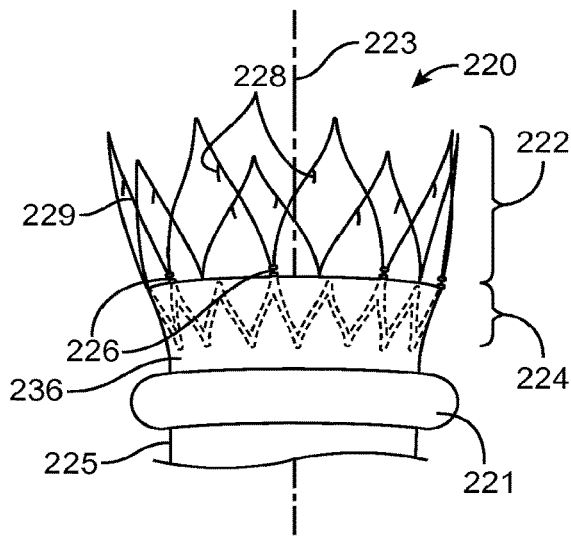
FIG. 4 shows an embodiment of a stent portion of a stent graft.

FIG. 4 shows an embodiment of a stent 220 of a stent graft 221 which includes a proximal portion 222 of the stent 220 and a distal portion 224 of the stent 220. Distal portion 224 in this case may be mechanically mated to a graft collar 236 of a graft body portion 225 of the stent graft 221 in any known manner or fashion—such as overlaying a layer of graft material and mating (as shown herein via sintering or the like), or by sewing the distal portion 224 onto the fabric material of the body portion of the stent graft. The material of the graft body portion 225 may be the same as discussed above with regard to stent graft 100. The graft body portion 225 may have a generally tubular configuration that extends along a longitudinal axis 223 of the stent graft 221. The stent graft 221 may also share other suitable materials, dimensions and features of stent graft 100 such as inflatable channels 106 and inflation sealing rings or cuffs 110 etc.

Proximal portion 222 of the stent 220 may be mated to the distal portion 224 via connection 226 (e.g. a dogbone structure) or may be made integrally with the distal portion. Optional barbs 228 may be constructed on the proximal portion 222 of the stent 220—the barbs 228 may be either welded or otherwise mechanically mated to the proximal portion 222. In other embodiments, barbs 228 may be made integrally with the proximal portion 222 of the stent 220 and may also be located on a strut 229 of the proximal portion 222 (as shown), or may be made at the apices of the proximal portion 222. The stents disclosed herein generally may be constructed out of any material suitable for this application—e.g. stainless steel, self-expanding metal such as superelastic alloys (NiTi or the like), etc.

Distal portion 224 of stent 220 may have a first axial length and proximal portion 222 of stent 220 may have a second axial length. As shown, the axial length of the proximal portion 222 is longer than the axial length of the distal portion 224. This may be advantageous in some cases where a patient has a challenging landing zone in the vessel 101—but in other cases, it may not be desirable from the standpoint of the stent's dynamic behavior in vivo. For example, in the case of a TAA, a stent graft 221 having a long proximal portion 222 might be subject to movement or hemodynamic forces that may cause injury to the patient's aorta due to movement of the proximal portion 222 against the patient's vasculature 101. In some embodiments, an axial length of proximal portion 222 may be about 20 mm to about 30 mm and an axial length of the distal portion 224 may be about 10 mm to about 15 mm. The proximal portion 222 may be secured to the distal portion 224 of the stent graft 221 by any suitable device or method. In some cases the attachment 226 may be an integral attachment, in some cases there may be a linked or mechanical attachment such as the dogbone type attachment shown in more detail in FIG. 5.

Figure 6:
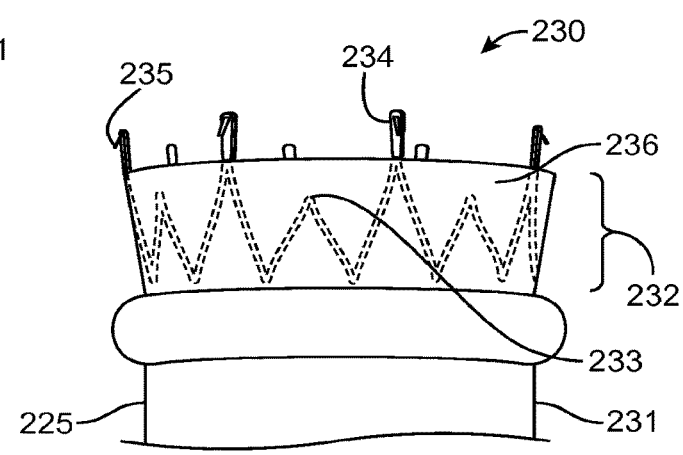
FIG. 6 shows an embodiment of a stent portion of a stent graft.

FIG. 6 shows another embodiment of a stent 230 of a stent graft 231 that may have desirable characteristics for providing good clinical performance in difficult anatomical conditions such as the anatomical conditions noted above including a highly angulated vessel configuration or difficult landing zone. For example, stent 230, which may be a self-expanding stent embodiment with a generally sinusoidal zig-zag configuration, may be configured to have an overall axial length that is less than an overall axial length of the stent 220 shown in FIG. 4. In addition, it may be possible to use either a short proximal portion or extension 234 extending proximally out from the graft collar 236 and distal portion 232—or no proximal portion 234 at all. In such cases, the barbs 235 of the stent might be substantially located at the top of graft collar 236. As shown in FIG. 6, it may be desirable for the number of proximal portions 234 to be some fractional proportion to the number of apices 233 of distal portion 232 (e.g. one half). In other embodiments, stent proximal portion or extension 234 may include different fractional proportions. In some embodiments, the short proximal portion or extension 234 may have an axial length on order of about 1 mm to about 14 mm, more specifically, about 1 mm to about 5 mm. The distal portion 232 may have an axial length on the order of about 10 mm to about 15 mm in some cases. In the case where the proximal portion 232 is about 1 mm or less in axial length, it may be considered that the proximal portion 234 may be just a barb 235 that sits atop the apices 233 of the distal portion 232 and may be just even with a top or proximal end of the graft collar 236.

In some embodiments of the stent graft 231, the stent graft 231 may include a graft body 225 including a flexible tubular main body having an inner lumen configured to confine a flow of fluid therethrough as shown in FIG. 6. The graft collar 236 may be disposed at a proximal end of the main body. The stent graft 231 may also include the stent 230 having a distal stent portion 232 which is disposed distally of a proximal edge of the graft collar 236. The distal stent portion 232 may be at least partially secured to the graft collar 236. In some cases, the entire distal stent portion 232 may be secured to the graft body at a position such as the graft collar 236. The distal stent portion 232 may be secured by any suitable means, including disposing the distal portion 232 between adjacent layers of material of the graft collar 236 or of the graft body 225 generally. The stent 230 may also include the proximal stent portion 234 which is disposed proximally of the graft collar 236 and may include at least one barb 235. The barb 235 may be extending generally in a distal direction and also extend somewhat radially outward from the proximal stent portion 234 and may have an axial length of about 1 mm to about 5 mm. In some instances, the proximal stent portion 234 includes a plurality of barbs 235 disposed proximally of the proximal edge of the graft collar 236. Self-expanding embodiments of the stent 230 and barbs 235 may include superelastic materials such as superelastic alloys including NiTi alloys and the like. In some cases, the stent graft 231 may have a stent 230 with a proximal portion 234 wherein no barbs are disposed more than about 5 mm from the proximal edge of the graft collar 236.

Figure 7:
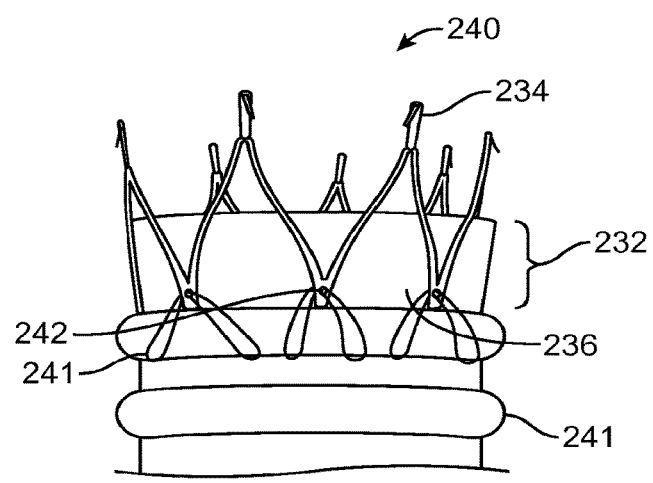
FIG. 7 shows an embodiment of a stent portion of a stent graft.

In some cases, the distal stent portion 232 may include a continuous sinusoidal configuration and the at least one barb 235 is disposed on a strut or extension of the proximal stent portion 234 that extends proximally from an apex of the sinusoidal configuration of the distal stent portion 232 as shown in FIG. 6. In other cases, the distal stent portion 232 may include a distal portion of a continuous sinusoidal configuration and the at least one barb may be disposed on a strut of a proximal portion 234 of the sinusoidal configuration that extends proximally from the proximal edge of the graft collar 236 and forms the proximal stent portion of the stent as shown in FIG. 14. In some instances, the stent 230 may include a balloon expandable stent that is made of a high strength biocompatible material that is subject to elastic deformation during radial expansion from a radially constrained state suitable for percutaneous delivery to an expanded deployed state suitable for engaging an inner luminal wall of a patient's vessel. Such high strength materials for balloon expandable stent construction may include high strength alloys such as stainless steel. Such stent embodiments, such as stent 230 or any other suitable stent embodiment discussed herein may include at least one eyelet on a distal portion of the stent and the distal portion of such a stent may be secured to a graft collar 236 or any other suitable portion of a graft body portion of a stent graft with a flap of flexible material that may be disposed through the eyelet and secured to the graft collar. Such a flap of material (as shown in FIGS. 7 and 14) may be secured to the graft collar or graft body by adhesive bonding, welding, sintering or the like.

Figure 27:
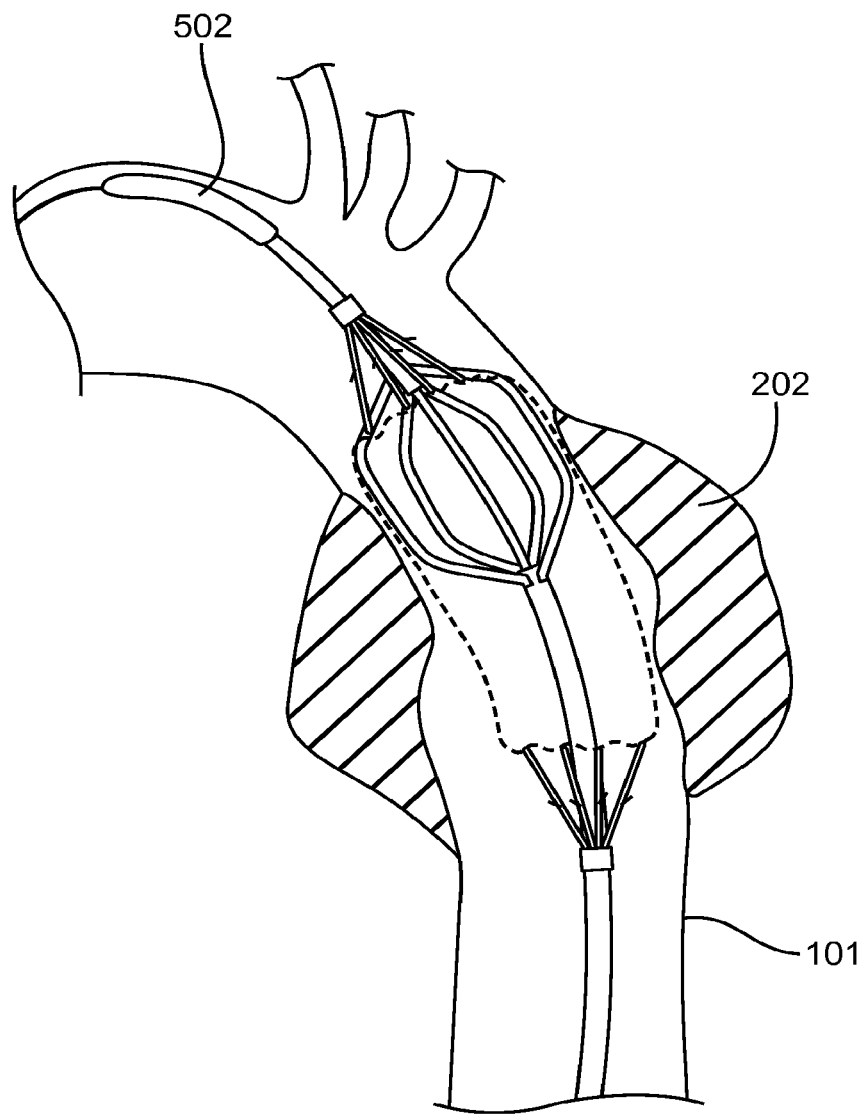
FIG. 27 shows the delivery catheter of FIG. 24 with the centering basket deployed within an inner lumen of a graft body section of a stent graft with proximal and distal stents partially deployed.

Some embodiments of a method of deploying such a stent graft in a patient's vessel 101 may include providing the stent graft 231 above. Thereafter, the stent graft 231 may be axially positioned at a desired site within the patient's vessel 101 (as shown in FIG. 27 and discussed below) with the at least one barb 235 disposed axially coextensive with a viable landing zone of the patient's vessel 101. The stent 230 may then be deployed so as to radially expand and physically engage the tissue of the viable landing zone of an inner luminal wall of the patient's vessel 101. In some cases, deploying the stent 230 may include deploying the stent disposed at a proximal end of the stent graft 231 disposed towards a source of blood flow in the patient's vessel 101, such as the patient's heart (not shown). In some instances wherein the stent 230 includes a self-expanding stent, deploying the stent 230 includes releasing a radial constraint from the stent 230 in a radially constrained state. In some embodiments wherein the stent 230 includes a balloon expandable stent, deploying the stent 230 includes expanding the stent 230 radially outward with an expandable member (not shown) disposed within an inner lumen of the stent 230. In some such cases, the expandable member may include an inflatable balloon and deploying the stent may include expanding the stent radially outward by inflating the inflatable balloon with a source of pressurized fluid.

In some embodiments, it may be desirable to have a stent of a stent graft (such as stent graft 100, stent graft 221, stent graft 231 or any other suitable stent graft discussed herein) that includes barbs (such as barbs 228, 235 or the like) that are disproportionately positioned and/or populated on one side of the stent. For example, in a highly angulated aorta 101, the top side of a stent graft may tend to take the brunt of the hemodynamic forces and pressures (being on the greater curve 208 of the aorta as shown in FIG. 2) than the side of the stent graft that lies along the lesser curve 206 of the aorta 101. In such a case, it may be desirable to configure a stent such that the top side portion of the stent includes more barbs (e.g. along every apices) and a lesser number or density of barbs along the low portion of the stent (e.g. to have barbs at every other apices).

In some cases, distal portion 232 of the stent 230 may be mated to the graft mechanically by encapsulating the metallic stent in between two or more layers of graft material and the graft layers mated or otherwise bonded together—e.g. between two layers of PTFE and sintered into place. The distal portion 232 could also be mated by sewing the distal portion to the graft materials of the graft body 225 or in any other known manner of mating or bonding layers.

FIG. 7 shows an embodiment of a stent graft 241 that may have similar features, dimensions and material with respect to stent graft 231, where a distal portion 232 of a stent 240 is mated to the graft collar 236 by using flaps of material 241 (e.g. PTFE) that are placed through eyelet 242. Fluorinated ethylene propylene (FEP) may be incorporated around eyelet 242 to improve the mating of the stent 240 to the graft collar 236. One advantage of using flaps of materials may be to improve the tensile strength of the retention of the stent 240 to the graft. The use of flaps may also reduce the amount of graft collar needed to anchor the stent 240. In some embodiments, the proximal portion 234 may have a length on order of about 5-15 mm and the distal portion 232 may have a length on order of about 5-15 mm.

FIGS. 8-11 show various embodiments of barbs that may be used for any suitable stent graft embodiment discussed in the present application. Barbs 260 may be placed at the apices of proximal portions (such as proximal portion 234 or distal portions 232, if there is no proximal portion 234) of stents or at the end of a strut or extension 262. The barb embodiments 260 and struts or extensions 262 may be disposed at either the proximal end or distal end of any suitable stent graft upon which they are used. Barbs 260 may be biased outward towards the tissue of an inner luminal surface of a patient's vessel 101 as shown in FIG. 3 to better engage the luminal surface of the patient's vessel 101, such as the aorta. In some embodiments, the barbs 260 may have a length extending from the strut of about 1 mm to about 5 mm.

Figure 8:
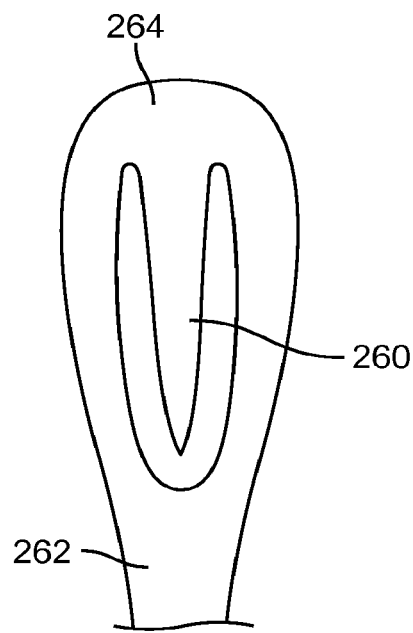
FIG. 8 shows an embodiment of a barb structure of a stent.
Figure 9:
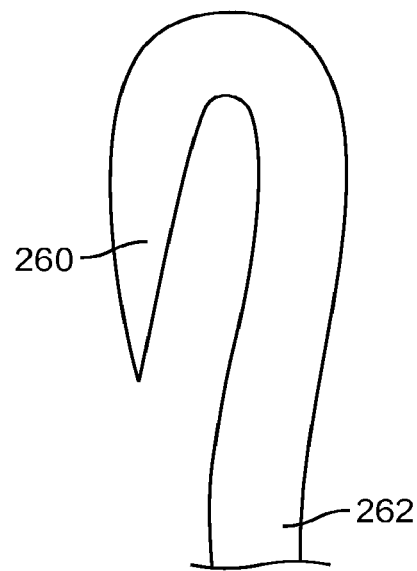
FIG. 9 shows an embodiment of a barb structure of a stent.
Figure 10:
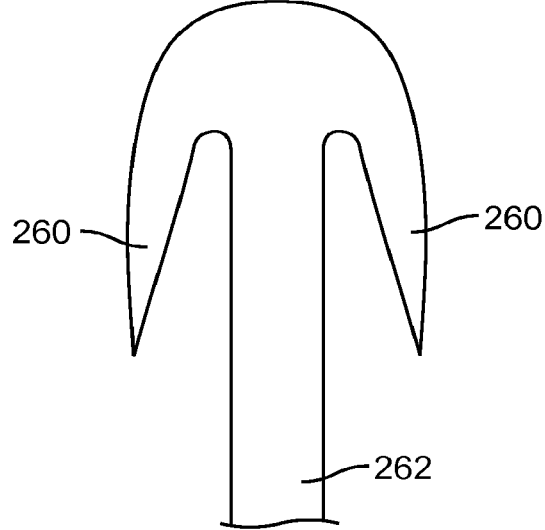
FIG. 10 shows an embodiment of a barb structure of a stent.
Figure 11:
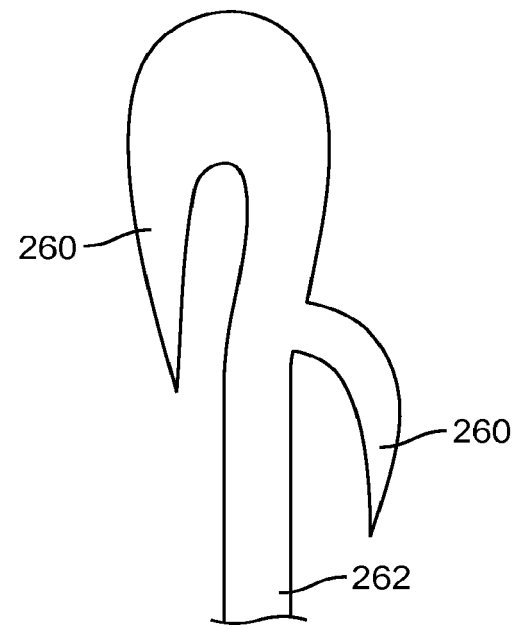
FIG. 11 shows an embodiment of a barb structure of a stent.

FIG. 8 shows a barb 260 that extends along a center line or longitudinal axis of strut 262 which has support legs extending to each side of the barb to a proximal most section or apex 264 from which the barb 260 extends. FIG. 9 illustrates a barb 260 that has a substantially hook shaped configuration wherein the barb is formed from an extension of the strut 262 which bends around in a u-turn and has a sharpened tip. In some cases, the strut 262 may be bent around in a u-turn at an angle of about 150 degrees to about 190 degrees. FIG. 10 illustrates a double-barb configuration wherein a strut 262 hooks around on two sides disposed opposite each other to form two barbs 260. Each barb 260 is formed by a u-shaped type pattern or configuration similar to the barb configuration shown in FIG. 9 but on two opposed sides of the strut. The barbs may extend distally along the strut 262 over a length of about 1 mm to about 5 mm, in some embodiments. FIG. 11 shows a double barb configuration similar to that of FIG. 10 with a first barb 260 on one side of the strut and a second barb 260 on an opposite side of the strut 262. However, in the embodiment of FIG. 11, a first barb 260 extends from a proximal apex of the strut and a second barb 260 extends from a position distal to the apex of the strut 262. In the embodiment shown, the second barb 260 extends from a position on the strut 262 that is substantially axially coextensive with the sharpened tissue penetrating point or tip of the first barb 260.

FIGS. 12 and 13 show embodiments of incorporation of the stent structure 230 within the graft material and configurations for securing the stent structure to the graft body. Dashed line 302 shown in FIGS. 12 and 13 represents a proximal boundary of a portion of the main graft where the inner lumen 107 defined by the main body of the stent graft is substantially cylindrical. Proximal of line or axial position represented by line 302 the inner lumen may begin to flare in a proximal direction to a larger inner luminal transverse dimension. In particular, graft collar 236 which is proximal of line 302, may be constructed to flare outwardly from line 302 in a proximal direction.

This flared configuration may be advantageous to help create a proper sealing of the aneurysm from the blood flow. This may be particularly the case when there is sufficient radial force provides by the stent to hold graft collar 236 against the luminal surface. FIG. 12 shown a stent graft embodiment having a configuration wherein a proximal sealing ring 304 (for example, sealing ring 304 could be an inflatable portion filled with a gel capable of hardening to provide a seal against blood flow) is distal of line 302. FIG. 13 depicts a similar sealing ring 304 that is configured to be proximal of, or straddling, line 302. It may be desirable in some cases to include a sealing ring 304 which is disposed proximal of line 302 because it may tend to allow for a shortening of the edge of graft collar 236. This may be useful for the treatment of patient having a shortened landing zone or area for securing mechanical attachment or fixation members of a stent, such as barbs or the like.

FIG. 14 depicts a somewhat flattened rendition of an embodiment of a stent portion 311. Although only a portion 311 of the stent is shown in the flattened illustration, the stent portion may be representative of a complete stent 300 having a typical configuration of the stents discussed herein generally with a substantially tubular or cylindrical shape with a stent element of high strength material extending about a longitudinal axis of the stent in a somewhat sinusoidal undulating pattern. For the embodiment shown in FIG. 14, anchoring of the stent 300 to a graft body section may be provided at least in part by flap material 306 threaded through eyelet 242 in a manner similar to that shown in the embodiment of FIG. 7. The flap material 306 may be selected to have a high tensile strength and bonding compatibility with the material of the graft body. In some cases, the flap 306 may include the same material as that of the main graft body. In some instances, such material may include Dacron®, PTFE or any other suitable material. Flap material 306 may be secured to the main graft body of the stent by adhesive bonding, such as with the use of FEP or the like, welding, sintering or any other suitable method. The flaps 306 may have a somewhat ribbon like configuration with a width that is substantially greater than the thickness of the flaps 306 in order to spread the tensile load imposed on the eyelet 242 over a greater area of the graft collar 236 or graft body generally. Barb 308 of stent 300, as shown, may be integrally constructed with the strut 311 such that there is no joint between the strut 313 and the barb 308 and the material of the strut extends continuously into the barb 308. Graft collar 236, after trimming excess material, may be defined by lines 302 to 310 in FIG. 14.

FIGS. 15-18 show various embodiments of radiopaque (RO) markers placed upon stent portions which may be used for any suitable stent embodiment discussed herein. As shown, the various RO markers may be placed as close to, straddling or proximal to, the top edge or proximal edge 402 of the graft collar 236 in order to better orient the device for the physician during implantation procedures. The RO markers 404 may be constructed of a wound or clipped elongate element or strand of NiTi, Pt, composite NiTi/Pt—Ir or NiTi/Au, Au or any other known biocompatible radiopaque materials. Markers 404 may be constructed in coil configuration made from coiled radiopaque wire or clip or any other known fashion. Markers 404 may be placed in an optional small transverse section of a dogbone structure 406 formed into the strut of a stent as shown in FIGS. 17 and 18 to maintain the position of the marker during manufacturing and loading into a delivery catheter. The dogbone structure includes a pair of opposed enlarged portions or shoulder portions of the strut of the stent with a reduced section therebetween. The elongate element may be wound or clipped to the reduced section so as to be mechanically captured between the shoulder portions of the dogbone 406. Any of the stent, barb, radiopaque marker, graft body section, inflatable channel, inflatable sealing ring embodiments or the like discussed herein may be included together in any suitable desired combination in an appropriate structure or configuration. In particular, any of the RO marker embodiments of FIGS. 15-18 may be used on any of the stent embodiments discussed herein. Any of the stent connection methods such as the use of flaps 306 as shown in FIGS. 7 and 14 may be used to connect any of the stent embodiments discussed herein to any suitable stent graft body section.

Various embodiments of delivery systems are discussed herein that may be adapted for the deployment of the stent graft systems discussed herein. FIG. 19 shows a catheter delivery system 500 which includes a delivery catheter 501 having a nosecone 502 which is placed initially into the patient percutaneously or by any other known vascular surgical technique. Nosecone 502 is at a proximal end of integral outer sheath 503 which may house any of the stent graft system embodiments discussed herein as well as any other suitable stent graft embodiment. Other parts of system 500 include a flush port 506 and handle 508 for the physician-operator to effect the deployment of the stent graft.

FIG. 22 shows an elevation view of a stent graft embodiment loaded onto delivery catheter system 500 with the graft portion of the stent graft not shown for clarity of illustration. Nosecone 502 is disposed at the proximal end of an elongate shaft 505 of the delivery catheter and is secured to a tubular member including a lumen (e.g. guide wire lumen 503). The stent 230 is shown having distal portion 232 and proximal portion 234 (without the graft material shown) loaded on the catheter and placed in proximity over an optional basket 504 which is coaxially disposed within the stent 230. Basket 504 may be constructed out of a self-expanding or super elastic metal e.g. NiTi (Nitinol) or the like. The basket 504 may include a plurality of struts or tines 504a.

Tines 504a may be shape set in any manner that is desirable to aid in the deployment of the stent graft. It will be appreciated that tines 504a may have one or more "humps" (e.g. camel hump feature, not shown) or the tines may be constructed to have helical or otherwise twisted orientation to each other. In some embodiments, both the stent 230 and the basket 504 may be loaded and secured via belts 506 and 508 respectively. Belts 506 and 508 may be actuated or deployed by the physician-operator via control means on the handle 508. The basket 504 and the stent 230 may also be constrained and loaded in any other suitable manner or fashion.

FIG. 23 depicts basket 504 after belt 508 has been released (or has otherwise been released from constraint). Basket 504, as deployed, defines a substantially symmetric opened configuration having a larger outer transverse dimension or diameter than the basket 504 in a constrained state as shown in FIG. 22. Not shown in FIG. 23 is that basket 504 is forcing the graft material of the stent graft in an opening biased position which is shown in FIG. 27. At this point, the physician-operator may release the belt 506 (or any other known restraining means or devices for the stent); thus allowing the stent 230 (if self-expanding) to expand and have the barbs (if any) engage the luminal surface of the patient's vessel 101.

Some embodiments of a delivery system for delivering a stent graft may include the delivery catheter 501 with an elongate shaft having a proximal section and a distal section. The system may also include a stent graft having a main graft body with an inner lumen configured for confining a flow of blood therethrough. The stent graft may be loaded on the proximal section of the delivery catheter 501 with the elongate shaft disposed within the inner lumen. In addition, the delivery system may also include the expandable centering device or basket 504 disposed on the elongate shaft within the inner lumen of the stent graft. The centering device 504 may be configured to expand from a radially contracted state as shown in FIG. 22 to a radially expanded state as shown in FIG. 23 for centering the elongate shaft and stent graft of the delivery system toward a midline or longitudinal axis 702 of a patient's vessel 101 when introduced into the patient's vessel 101. In some cases, the centering device may include and expanding basket such as expanding basket 504.

In some cases, the basket may include the elongate tines 504a that extend substantially parallel to the elongate shaft of the delivery catheter in the radially contracted configuration as shown in FIG. 22. The elongate tines 504a may also be configured to bow radially outwardly from the elongate shaft in a substantially concentric arrangement in the radially expanded configuration as shown in FIG. 23. In some cases, the elongate tines are configured to self-expand to the radially expanded configuration and in some cases the elongate tines are configured to expand to the radially expanded configuration due to axial compressive force applied to at least one end of the tines. For the self-expanding embodiments, the elongate tines may include a self-expanding or superelastic metal such as a NiTi alloy. Some embodiments of the centering device may have an outer transverse dimension of about 50 mm to about 80 mm in the radially expanded state and may be configured to expand to an outer transverse dimension that is at least as large as an inner transverse dimension of the inner lumen of the patient's vessel 101.

FIGS. 24-26 show a dynamic operation and deployment of basket 504 during a deployment sequence of the stent graft. In some instances, the delivery catheter 501 may be positioned within a patient's vessel 101 such that the stent graft is axially positioned at a desired site within the patient's vessel 101 as shown in FIG. 27. The expandable centering device may be in the radially contracted state during the positioning process in some cases. The expandable centering device may then be expanded to the radially expanded state to center the elongate shaft and stent graft of the delivery system toward the longitudinal axis 702 of the patient's vessel 101. In addition, the stent 230 of the stent graft may then be deployed so as to engage an inner luminal wall of the patient's vessel. FIG. 24 shows the catheter 501 inserted into a vessel 101 of a patient having a TAA condition 202. As shown, the delivery catheter 501 would tend to lie along the greater-curve 208 of the aorta because of the mechanical stiffness of the catheter. It will be appreciated, however, that due to variations in patient anatomy and geometry that the delivery catheter 501 might also tend to lie along the lesser-curve, instead of the greater-curve. In some cases however, it may be desirable to have the catheter move and lie more along the midline or longitudinal axis 702 of the aorta prior to device deployment of the stent graft from the delivery catheter 501.

Nosecone 502 is shown also along greater-curve 208. Midline 702 shows the middle of the thoracic region of the aorta 101 itself. If the stent graft were to be deployed with the catheter as shown in FIG. 24, there is a possibility that the stent and the graft portions of the stent graft may not deploy in a desirable manner. For example, the stent portion might miss the desired landing zone and there may be some undesirable positioning of graft material due to an asymmetric deployment which might compromise the integrity of the later-filled sealing rings in producing a sufficient seal and exclusion of the aneurysm 202 from blood flow.

FIG. 26 shows how an expandable basket 504 may alleviate some of these undesirable conditions. Basket 504, as deployed, may help to center the stent graft along midline 702 prior to deployment of the stent portion and subsequent filling of inflation rings in the graft material. In some instances, deploying the stent may include deploying a stent disposed at a proximal end of the stent graft disposed towards a source of blood flow in the patient's vessel 101. In some embodiments wherein the expandable centering device includes a basket 504, expanding the expandable centering device may include allowing self-expanding elongate tines 504a of the basket 504 to self-expand to the radially expanded state. In some embodiments expanding the expandable centering device includes axially compressing at least one end of elongate tines 504a of the basket 504 to shorten a separation of the proximal ends and distal ends of the elongate tines 504a of the basket 504 and expand a center portion of the tines 504a to the radially expanded state. In some cases, expanding the expandable centering device to the radially expanded state to center the elongate shaft and stent graft of the delivery system toward the longitudinal axis of the patient's vessel 101 may include expanding the expandable centering device, such as basket 504, or balloon 710 discussed below, to an outer transverse dimension which is about the same as a transverse dimension of an inner lumen of the patient's vessel 101 at a position of the expandable centering device.

Some centering device embodiments may also include an inflatable structure such as the inflatable structure 710 shown in FIG. 28. The inflatable structure 710 may have a collapsed deflated state (not shown) and an enlarged inflated state as shown in FIG. 28. In some cases, in the enlarged inflated state, the centering device 710 may have a substantially cylindrical configuration including vias that extend from ports 714 in a proximal surface of the centering device 710 to respective ports in a distal surface of the centering device. The vias 714 may be configured to provide for continuous flow of blood through the inflatable centering device and delivery system during inflation of the centering device and deployment of the stent graft. In some cases, the expandable vias have a cumulative cross section that is at least about 5 percent to about 10 percent of the total cross section of the centering device in an expanded state. In some instances, the expandable centering device may include a configuration that is radially concentric with the elongate shaft in the enlarged inflated state.

FIG. 28 shows an embodiment of an inflatable balloon 710 which may be used in place of or in addition to basket 504 and which serves to aid the catheter to tend toward midline 702 of the patient's vessel 101 prior to deployment. Balloon 710 includes a plurality of films or layers of flexible material that may be hermetically sealed together or otherwise joined to form a fluid tight interior volume that once inflated may assume an annular or circular shape. The balloon 710 may also include a structure or structures that allow blood to flow therethrough. For some embodiments, via holes or vias 714 may pass from a proximal end of the balloon 710 to a distal end of the balloon 710 at a radial position disposed inwardly of the outer radial surface of the balloon 710. The vias 714 may extend from a port on a proximal surface of the balloon 710 to a respective port on a distal surface of the balloon 710. Balloon 710 may be mated to an elongated tubular member 712 by any suitable method or means, in particular, via adhesives or the like. The elongated tubular member 712 may have an inner lumen 713 that may be used to accommodate a guidewire or the like as shown in FIG. 29.

Figure 30:
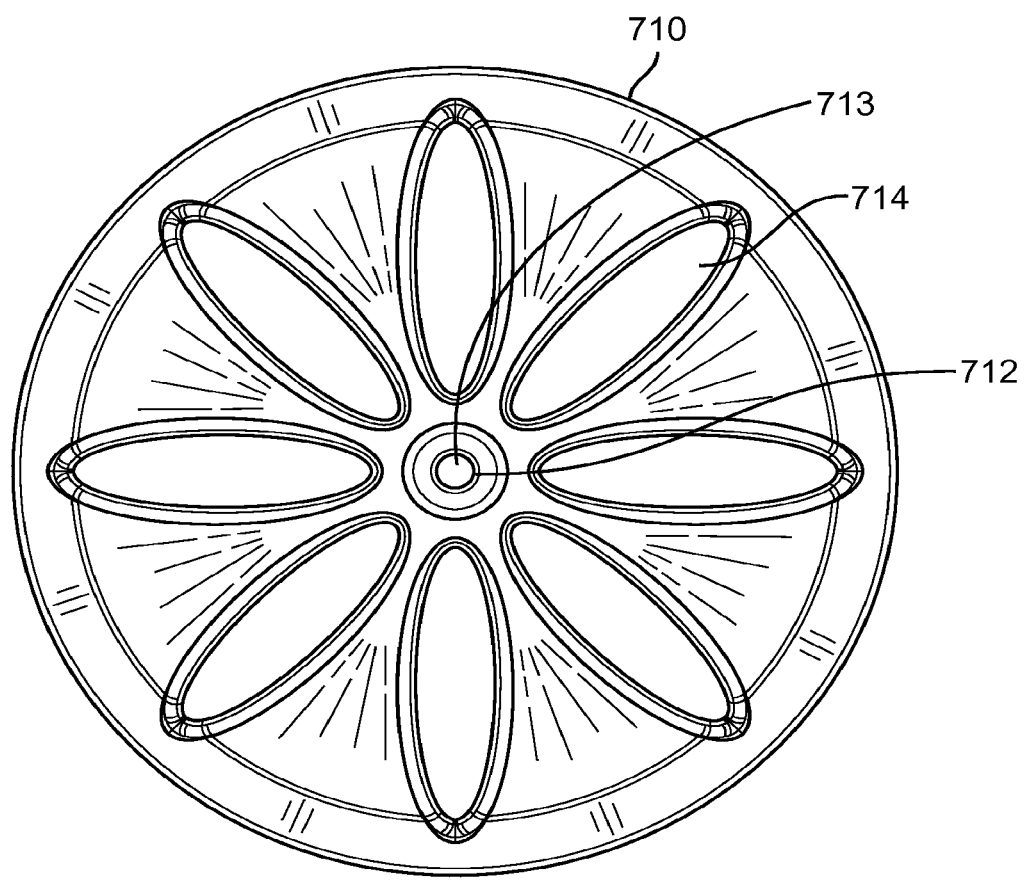
FIG. 30 is an end view of the inflatable structure of FIG. 28.

Ports (not shown on elongated tubular member 712) in fluid communication with an interior volume of the balloon 710 and with an inflation lumen 715 may be used to inflate balloon 710 with air, gas or liquid or the like. The inflation of balloon 710 may be carried out by injection of an inflation fluid from a source of pressurized fluid 716, through supply lumen 717, through inflation lumen 715 and into the interior volume of the balloon 710. FIG. 30 is an end view of balloon 710 once inflated illustrating the vias. There may be other devices to effect the centering of the delivery catheter 501 prior to deployment and embodiments of the present invention encompass all such known means and devices. It may be merely desirable that the delivery catheter 501 be induced to lie more along the midline or longitudinal axis 702 of the aorta prior to device deployment. In some cases, expanding the expandable centering device may include inflating an interior volume of the inflatable structure with a biocompatible fluid to expand the inflatable structure to the radially expanded state. For some embodiments, the interior volume of the inflatable structure may be inflated through an inflation lumen with a fluid from a source of pressurized fluid. The source of pressurized fluid may include a syringe for some embodiments and inflating the interior volume of the inflatable structure may include injecting fluid from an interior volume of the syringe through the inflation lumen and into the interior volume of the inflatable structure. Any suitable inflation fluid may be used for inflating the interior volume of the inflatable structure including biocompatible fluids such as saline solution.

Figure 31:
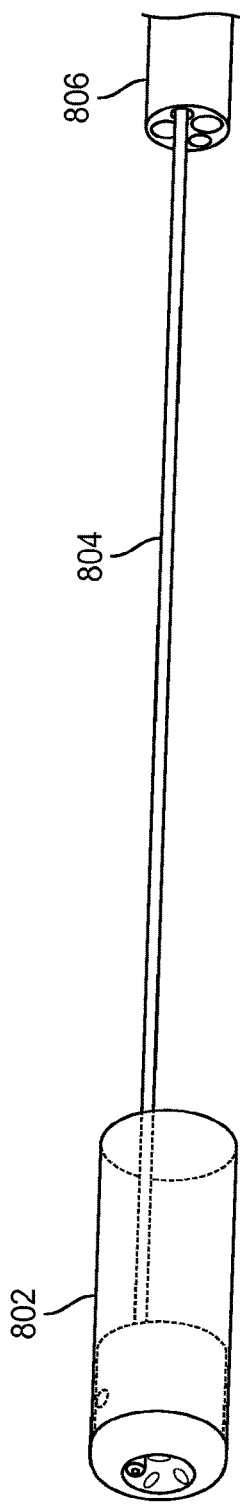
FIG. 31 shows a perspective view of a portion of an embodiment of a delivery catheter that includes a sleeve coupled to a multi-lumen shaft by a push rod.
Figure 32:
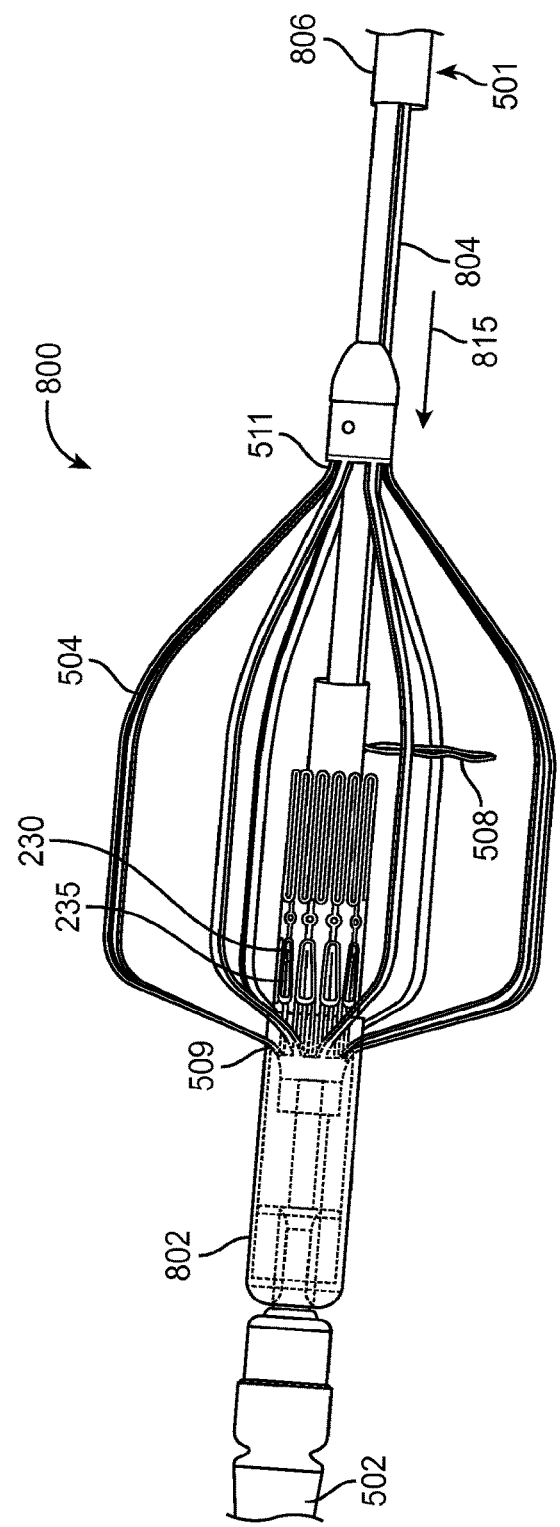
FIG. 32 is an elevation view of a section of a delivery catheter than includes an expandable member having a basket configuration with the basket in a shortened and radially expanded state.

FIGS. 31 and 32 illustrate an embodiment of a deployment structure 800 for the stent 230 or any other suitable stent of a stent graft discussed herein which may be incorporated into a delivery system having a delivery catheter such as delivery catheter 501. The main graft body of the stent graft loaded onto the delivery catheter is not shown in FIG. 32 for purposes of clarity of illustration. The delivery catheter 501 shown in FIG. 32 may include many of the same features, dimensions and materials as those of the delivery catheter embodiments 501 discussed herein. As shown in FIGS. 31 and 32, sleeve 802 is slidably disposed over the elongate shaft of the delivery catheter 501 and may be configured to surround and constrain barbs 235 once the stent 230 is loaded into delivery catheter 501 and the sleeve is disposed in a distal position covering the barbs 235 of the stent 230. The physician-operator may deploy basket 504 as described herein by shortening the separation of the proximal ends 509 of the tines of the expandable basket relative to the distal ends 511 of the tines of the elongate basket 504. Thereafter, an axial force, in a proximal direction as indicated by arrow 815, may be applied to push rod 804 which may be slidably disposed within or adjacent an elongate multi-lumen structure or shaft 806. Once sleeve 802 is pushed proximally beyond mechanical mating with or radial constraint of barbs 235, the stent portion would deploy in an outward radial direction.

Figure 36:
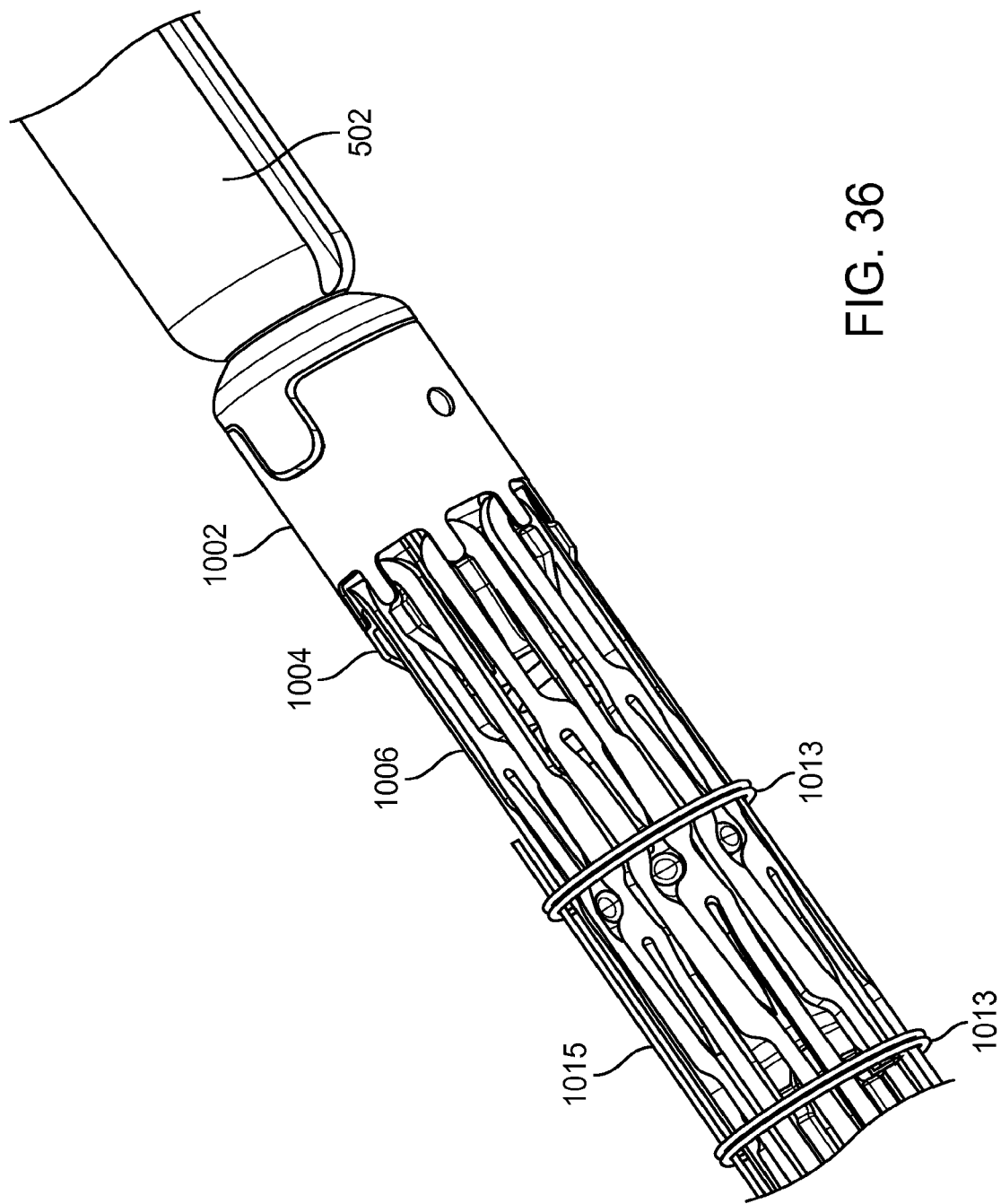
FIG. 36 is a perspective view of the stent constraint system of FIG. 35 with the stent shown in a radially constrained state loaded onto the delivery catheter and held in place by the constraint system.

FIGS. 33 and 34 show yet another embodiment of the delivery system 500 which is configured to deploy stent graft embodiments discussed herein. FIGS. 33 and 34 do not show the main graft body of the stent graft for purposes of clarity of illustration. FIG. 33 shows the stent graft as loaded onto the delivery catheter 501 in a radially constrained state suitable for percutaneous delivery through the vessels 101 of a patient's body. In this embodiment, there are shown multiple belt/constraints for both stent 902 and basket 504— with belts 506a and 506b being disposed about and radially constraining self-expanding stent 902 and belts 508a and 508b disposed about and radially constraining basket 504. FIG. 34 shows the belts 508a and 508b released from constraint of the basket 504 which is shown in a radially expanded state with a shorter axial separation between proximal and distal ends 509 and 511 relative to the axial separation shown in FIG. 33. The belts 508a and 508b may be held or locked into a constraining configuration by a trigger wire (not shown) and deployed by retraction of the trigger wire as shown in FIG. 36 and discussed below. In some cases, a physician-operator may deploy basket 504 in stages via belts 508a and 508b for a more accurate and controlled deployment.

In some cases, an operator may also wish to deploy stent 902 in stages for a more accurate placement or better control of the stent deployment. In particular, FIG. 34 shows the partial deployment of stent 902 wherein a first belt 508a and a second or final constraint or belt 508b has been released from a constraining configuration with the retraction of a trigger wire or any other suitable means. However, a stent crown constraint 915 which may have features and/or mode of operation similar to those of constraint 1000 shown in FIG. 35 and discussed below, has yet to be actuated or released—which may allow for repositioning of the stent graft by the physician under fluoroscopy. Thereafter, an operator may deploy constraint 915 to completely deploy stent 902. The belts 508a, 508b, 506a and 506b may also be deployed or released in any desired order or sequence in order to achieve a desired partially deployed state of either the basket 504 or the stent 902.

Figure 35:
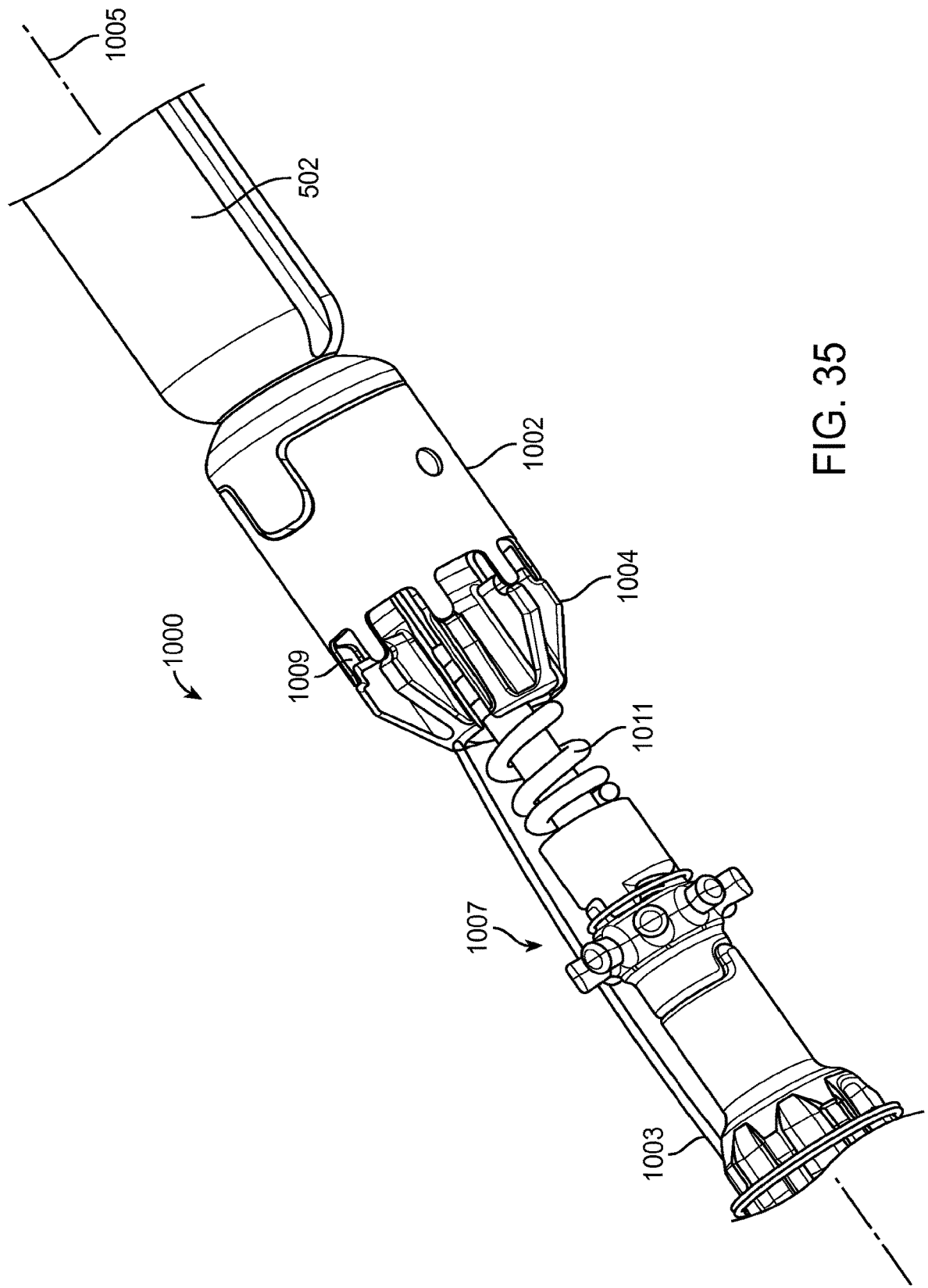
FIG. 35 is a perspective view of a portion of an embodiment of a stent constraint system with the stent of a stent graft not shown for purposes of illustration.
Figure 37:
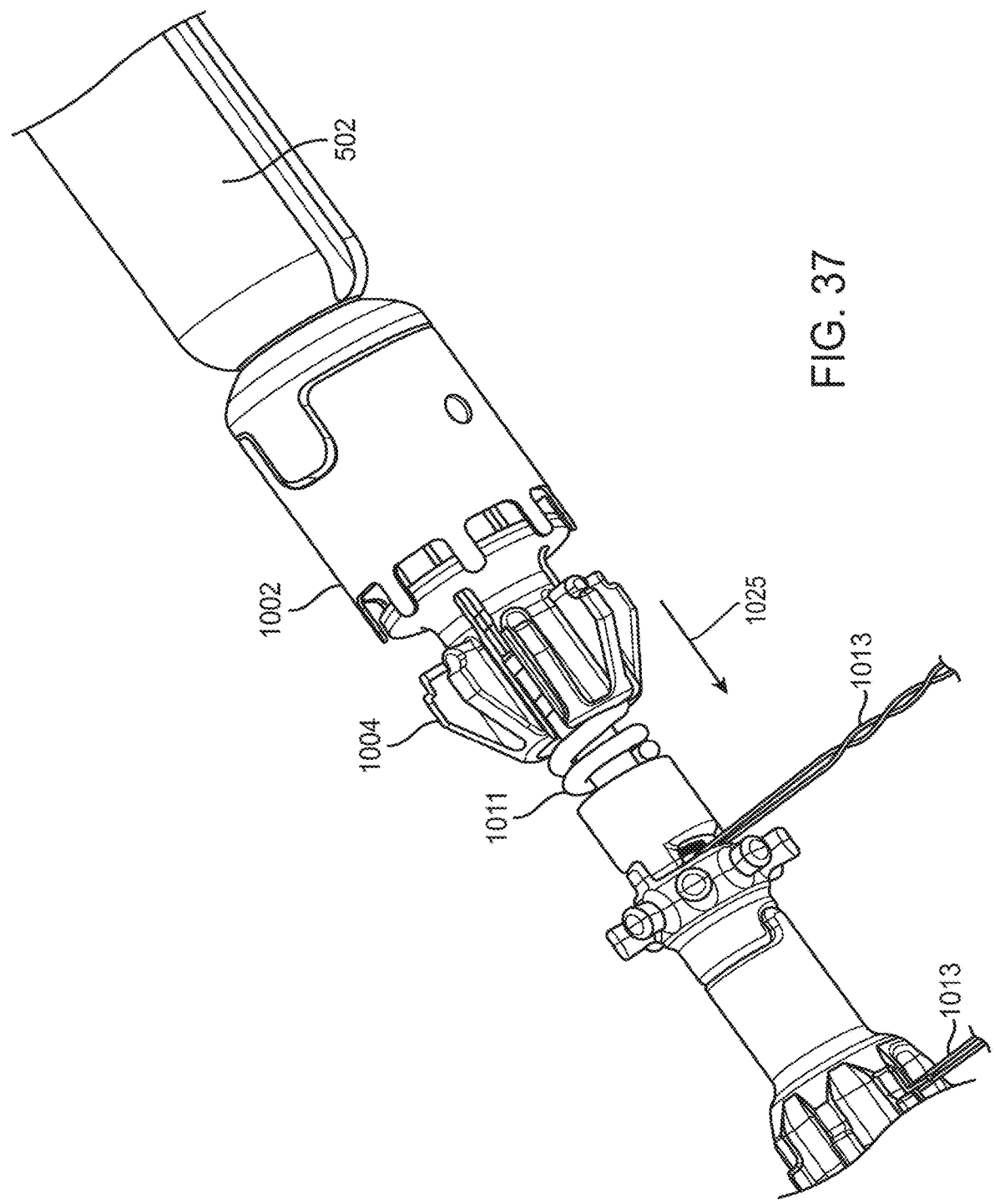
FIG. 37 is an elevation view of the constraint system of FIG. 36 with the stent deployed from the constraint system.

FIGS. 35-37 depict an embodiment of loading a stent of a stent graft onto a delivery catheter of a delivery system. Constraint system 1000 comprises a crown constraint sleeve 1002 and strut support assembly 1004. In FIG. 35, both crown constraint 1002 and stent support assembly 1004 are shown as they would be configured in a docket position, constraining a stent (without the stent shown for purposes of illustration). FIG. 36 shows the same configuration but with stent 1006 loaded and constrained by constraint system 1000. FIG. 37 shows the configuration of constraint system 1000 upon removing the constraint imposed by the constraint system 1000 on the stent 1006 and deploying the stent in a vessel lumen 101 of the patient. It may be seen that strut support assembly 1004 has moved distally in the direction of arrow 1025 with respect to crown constraint sleeve 1002 via a pull wire 1003, push rod, spring action or any other known manner of effecting slidable coupling. After deployment, it is desirable that crown constraint 1002 and strut support assembly 1004 reconnect, so as to not capture or engage with the tissue of a patient's vessel 101. Belts are also shown released and extending radially from delivery catheter.

Some embodiments of a delivery system for delivering a stent graft include the delivery catheter 501 having an elongate shaft with a proximal section and a distal section. The delivery catheter 501 may also include the releasable stent constraint system 1000 disposed on the proximal section elongate shaft. In some cases, the stent constraint system 1000 may include the crown constraint sleeve 1002 having a rigid tubular structure disposed about the elongate shaft with a plurality of crown restraint extensions extending distally from the crown constraint sleeve 1002. The crown restraint extensions may generally be circumferentially spaced from each other. The catheter 501 may also include the strut support assembly 1004 which is slidingly disposed about the elongate shaft distally adjacent the crown constraint sleeve 1002. The strut support assembly 1004 may include a plurality of the strut supports which are circumferentially aligned with respective crown restraint extensions of the crown constraint sleeve 1002 and which extend radially away from a longitudinal axis 1005 of the elongate shaft 1007.

The constraint system has a docked state wherein the strut supports form closed but openable crown constraint passages 1009 between the strut supports and respective crown constraint extensions of the crown constraint sleeve 1002. The constraint system also includes an open state wherein the strut support assembly 1004 is spaced axially away from the crown constraint sleeve 1002 and the crown restraint passages are opened to allow radial expansion of stent crowns disposed therein. The delivery system may also include a stent graft including a self-expanding stent 230 secured to a proximal end of a main graft body. In some cases, the main graft body may have an inner lumen configured for confining a flow of blood therethrough. The stent graft is loaded on the proximal section of the delivery catheter 501 with the elongate shaft 1007 disposed within the inner lumen and a plurality of proximal stent crowns disposed within closed crown restraint passages 1009 of the stent constraint system 1000. So configured, the strut support assembly 1004 is in a docket state.

In some cases, the crown constraint sleeve 1002 may be secured to the elongate shaft 1007 and the strut support assembly 1004 may be slidingly disposed about the elongate shaft 1007 distally adjacent the crown constraint sleeve 1002. In addition, such a strut support assembly 1004 may be resiliently biased towards the crown constraint sleeve 1002 in an axial direction. In some instances, the strut support assembly 1004 may be resiliently biased towards the crown constraint sleeve 1002 in an axial direction by an axially oriented spring 1011 disposed between the strut support assembly 1004 and the elongate shaft 1007. For some other embodiments, the strut support assembly 1004 may be secured to the elongate shaft 1007 and the crown constraint sleeve 1002 may be slidingly disposed about the elongate shaft 1007 proximally adjacent the crown constraint sleeve 1002. In some cases, the delivery system may also include at least one releasable belt 1013 disposed about the stent 1006 of the stent graft. The at least one releasable belt 1013 may be locked in a constrained configuration about the stent 1006 with a removable trigger wire 1015 that may be axially retracted in order to release the constrained belts which are mechanically captured in a constraining configuration by the trigger wire 1015.

In use, a stent graft loaded on a delivery catheter having such a constraint system 1000 may be axially positioning at a desired site within the patient's vessel 101 as shown in FIG. 27. Thereafter, the crown restraint sleeve 1002 may be axially separated from the strut support assembly 1004 so as to open the crown restraint passages 1009 allowing crowns of the stent 1006 contained within the crown restraint passages 1009 to radially expand. In some instances, the crown constraint sleeve 1002 may be secured to elongate shaft 1007 and the strut support member 1004 may be slidingly disposed about elongate shaft 1007 distally adjacent the crown constraint sleeve 1002. In such a case, axially separating the crown restraint sleeve 1002 from the strut support assembly 1004 so as to open the crown restraint passages 1009 allowing crowns of the stent 1006 contained within the crown restraint passages 1009 to radially expand may include displacing the strut support member 1004 in an axial direction relative to the crown constraint sleeve 1002 and the elongate shaft 1007. In some cases, the strut support assembly 1004 may be secured to the elongate shaft 1007 and the crown constraint sleeve 1002 is slidingly disposed about elongate shaft 1007 proximally adjacent the crown constraint sleeve 1002. In such an embodiment, axially separating the crown restraint sleeve 1002 from the strut support assembly 1004 so as to open the crown restraint passages 1009 allowing crowns of the stent 1006 contained within the crown restraint passages 1009 may include displacing the crown constraint sleeve 1002 in a proximal direction relative to the strut support assembly 1004 and the elongate shaft 1007.

In some cases, the crown constraint sleeve 1002 may be secured to the elongate shaft 1007 and the strut support member 1004 may be slidingly disposed about elongate shaft 1007 distally adjacent the crown constraint sleeve 1002. In such a case, axially separating the crown restraint sleeve 1002 from the strut support assembly 1004 so as to open the crown restraint passages 1009 allowing crowns of the stent 1006 contained within the crown restraint passages 1009 to radially expand may include displacing the strut support member 1004 in an axial direction relative to the crown constraint sleeve 1002 and the elongate shaft 1007. For such embodiments, the strut support assembly 1004 may be resiliently biased towards the crown constraint sleeve 1002 in an axial direction and displacing the strut support assembly 1004 in an axial direction relative to the crown constraint sleeve 1002 and the elongate shaft 1007 may include retracting the strut support assembly 1004 by applying axial displacement in a distal direction on a pull rod or pull wire 1003 that is secured to the strut support assembly 1004 and extends distally to a distal end of the elongate shaft 1007.

In some cases (not shown), the strut support assembly 1004 may be secured to the elongate shaft 1007 and the crown constraint sleeve 1002 may be slidingly disposed about elongate shaft 1007 proximally adjacent the crown constraint sleeve 1002. For such an embodiment, axially separating the crown restraint sleeve 1002 from the strut support assembly 1004 so as to open the crown restraint passages 1009 allowing crowns of the stent 1006 contained within the crown restraint passages 1009 may include displacing the crown constraint sleeve 1002 in a proximal direction relative to the strut support assembly 1004 and the elongate shaft 1007. In such a case, the crown constraint sleeve 1002 may be resiliently biased towards the strut support assembly 1004 in an axial direction and displacing the crown constraint sleeve 1002 in an axial direction relative to the strut support member 1004 and the elongate shaft 1007 may include displacing the crown constraint sleeve 1002 by applying axial displacement in a proximal direction on a push rod (not shown) that is secured to the crown constraint sleeve 1002 and extends distally to a distal end of the elongate shaft 1007.

Figure 38:
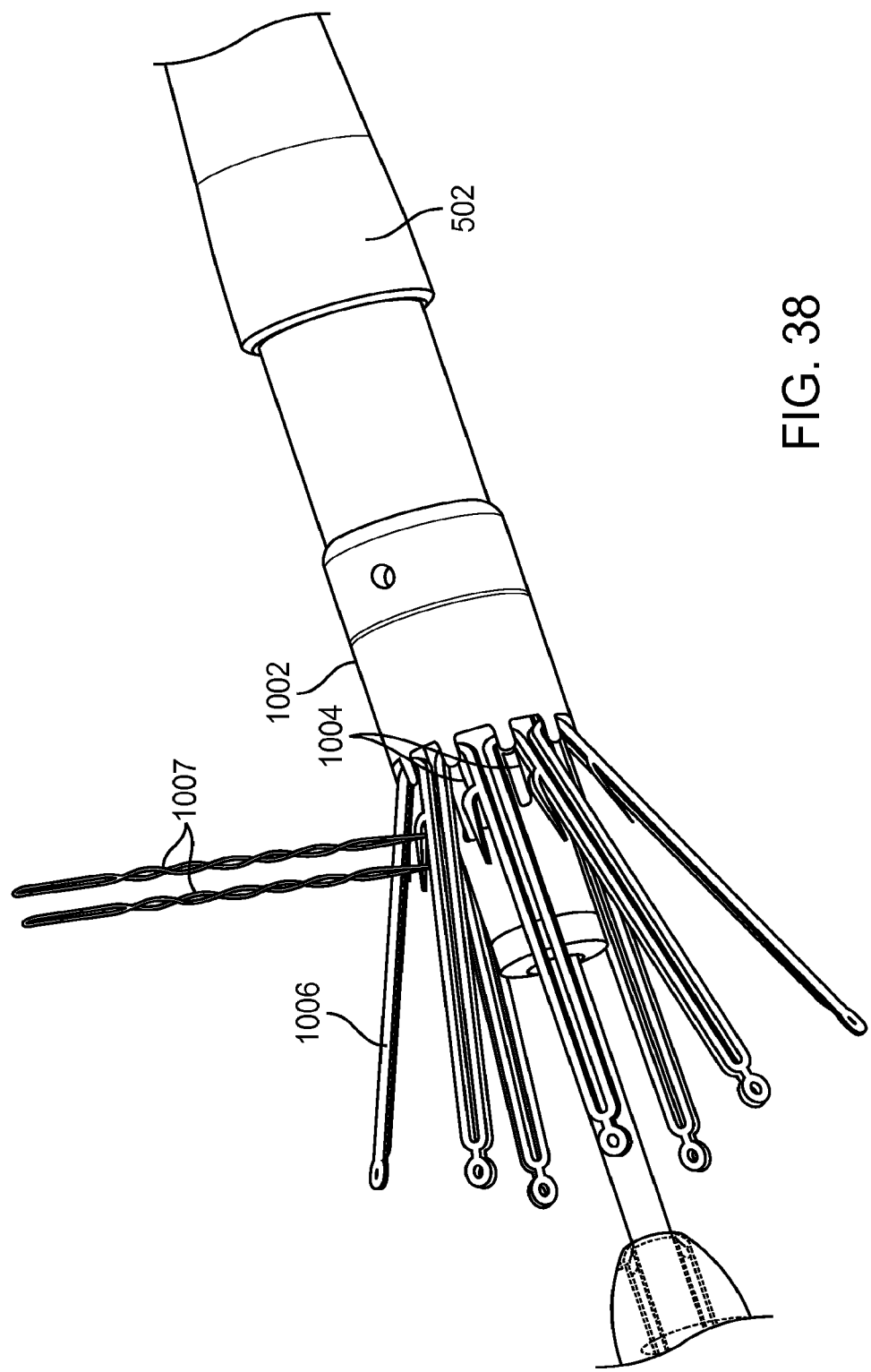
FIG. 38 is a perspective view of a portion of an embodiment of a stent constraint system with a stent in a partially deployed state and a graft body of the stent graft not shown for purposes of illustration.

FIG. 38 illustrates an embodiment of loading the constraint system 1000 shown in FIGS. 35-37 which may be incorporated into any suitable delivery system discussed herein. In this embodiment, strut support 1004 is held rigidly with respect to the delivery catheter 501 and crown constraint sleeve 1002 is slidably attached to the delivery catheter 501 and, upon removing of the constraint of the stent, crown constraint sleeve 1002 is moved proximally with respect to the catheter. Additionally, stent 1006 is shown flared out in the distal portion due to release of a first belt constraint 1007. The slidable movement of crown constraint sleeve 1002 may be accomplished after physician-operator has an opportunity to reposition the delivery catheter 501 within the vessel 101 of the patient with the aid of visualization such as by fluoroscopy.

Figure 39:
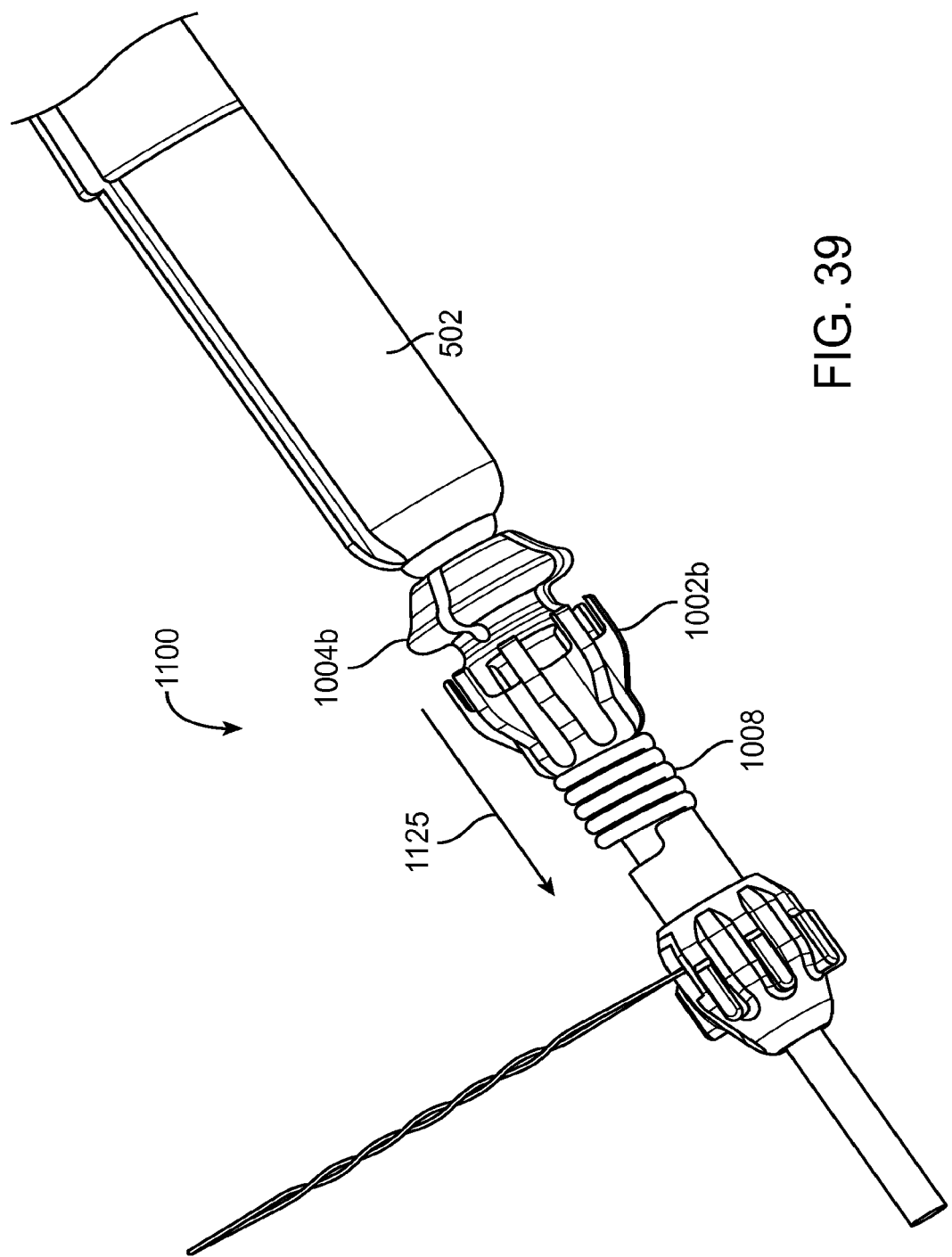
FIG. 39 is a perspective view of the stent constraint system of FIG. 38 with the stent fully deployed.

FIG. 39 shows an embodiment of a constraint system 1100 for loading any suitable stent discussed herein and which may be incorporated into any suitable delivery system discussed herein. FIG. 39 shows a constraint configuration after release and deployment of the stent. Crown constraint assembly 1002b has been moved slidably in a distal direction as shown by arrow 1125 relative to support structure 1004b. Return spring 1008 is used to dock crown constraint assembly 1002b to support 1004b to radially constrain the proximal stent crowns of the stent graft. The crown constraint assembly may be axially displaced as shown by a pull wire 1003 as shown in FIG. 35 and discussed above. The crown constraint assembly 1002b includes proximally extending crown elements which are circumferentially spaced from each other and configured to form openable constraint apertures similar to apertures 1009 shown in FIG. 35 when the assembly 1002b is axially engaged with support structure 1004b.

Figure 40:
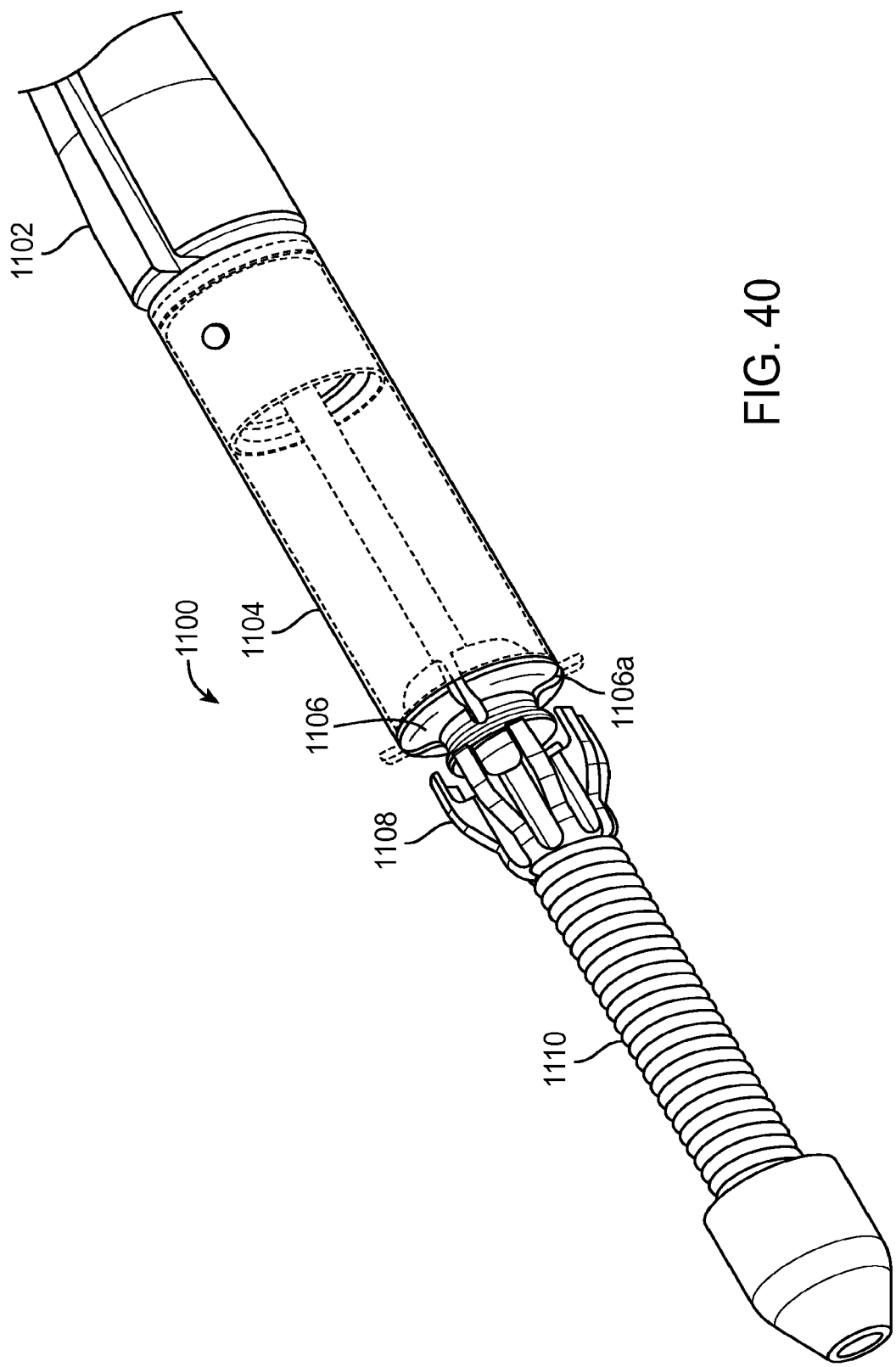
FIG. 40 is a perspective view of a portion of an embodiment of a stent constraint system with a sleeve thereof in a proximal position.

FIGS. 40-44 show an embodiment of a constraint system for loading a stent of a stent graft, including any suitable stent or stent graft embodiments discussed herein. The constraint system may also be incorporated into any suitable delivery system discussed herein. Nosecone 1102 is the proximal most portion of the delivery catheter and is mated to sleeve 1104. Sleeve 1104 provides the constraint for the stent and the barbs, together with support 1106 and crown constraint assembly 1108. Spring 1110 provides a mechanism for the mating/de-mating of crown constraint assembly 1108 and support 1106. FIG. 40 shows the configuration of the constraint system immediately after the stent has been fully deployed into the patient.

Figure 41:
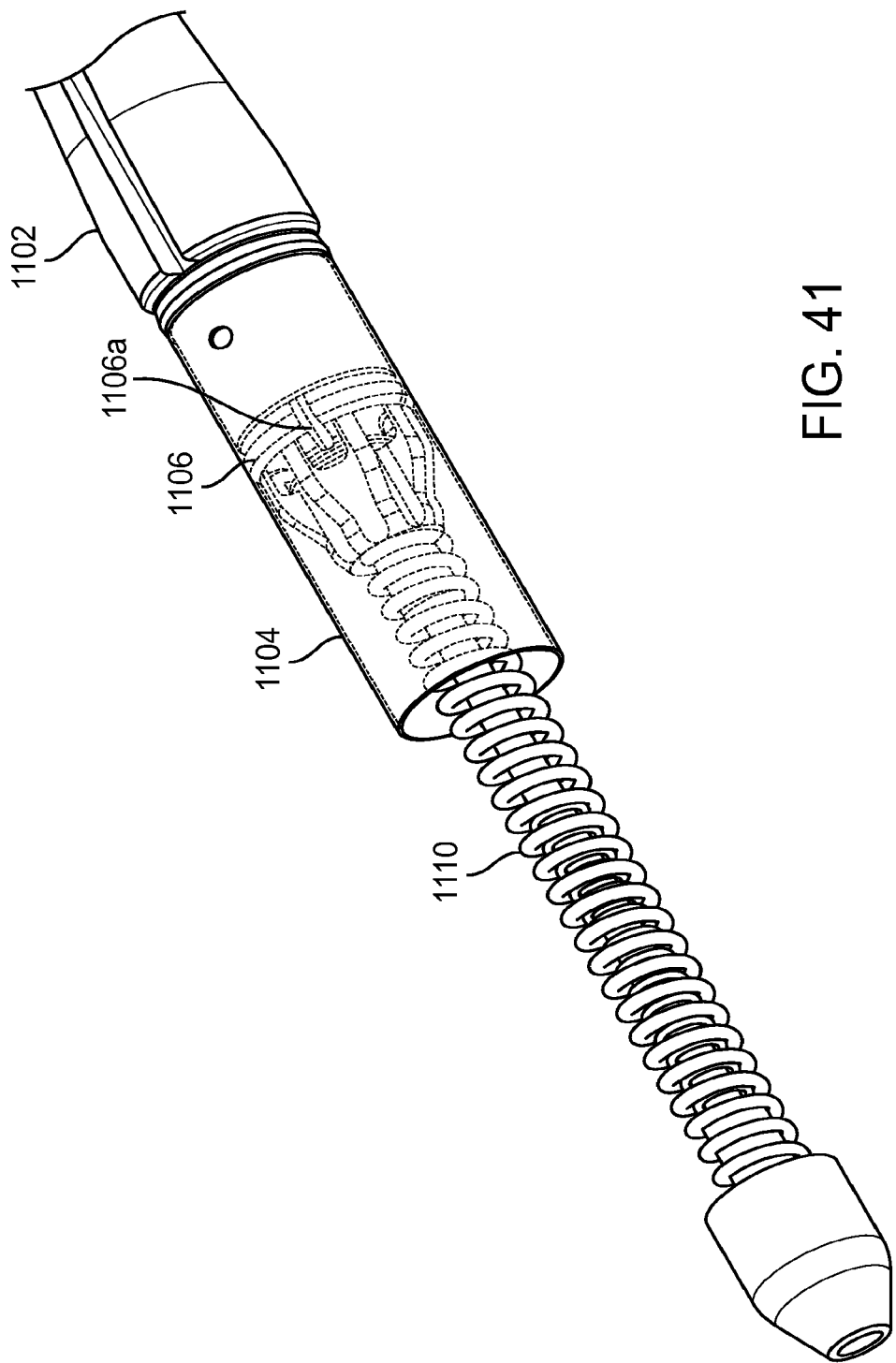
FIG. 41 is a perspective view of the constraint system of FIG. 40 with the sleeve displaced distally relative to the position of a support and crown constraint assembly shown in FIG. 40.

FIG. 41 shows the constraint in a configuration such as would be the case with the stent loaded (stent not shown) and prior to release of any constraint. It should be noted that support 1106 has cantilevered portions 1106a that may be spring loaded so that when support 1106 is inside sleeve 1104 the cantilevered portions are compressed to a smaller dimension and when support 1106 is moved distally from sleeve 1104 (as shown in FIG. 35), then the cantilevered portions expand as shown by the dashed lines of 1106a in FIG. 35; thus not allowing the support 1106 to return inside sleeve 1104.

FIGS. 42 through 44 show a sequence of figures whereby the stent is released from a constrained configuration. FIG. 42 shows the configuration where the stent is fully loaded prior to deployment. FIG. 43 shows the configuration where the support 1106 and crown 1108 have been moved relative with respect to sleeve 1104. In this configuration, stent (not shown) has its distal portion flared outward; but the apices of the stent and barbs are still constrained by crown 1108 and support 1106 which are axially pushed together to confine the proximal crowns of the stent. FIG. 44 shows the configuration immediately after full deployment of the stent wherein the crown 1108 has been moved distally relative with respect to support 1106 to open a gap between the support 1106 and the crown constraint assembly 1108 to allow the stent to self-expand.

Figure 45:
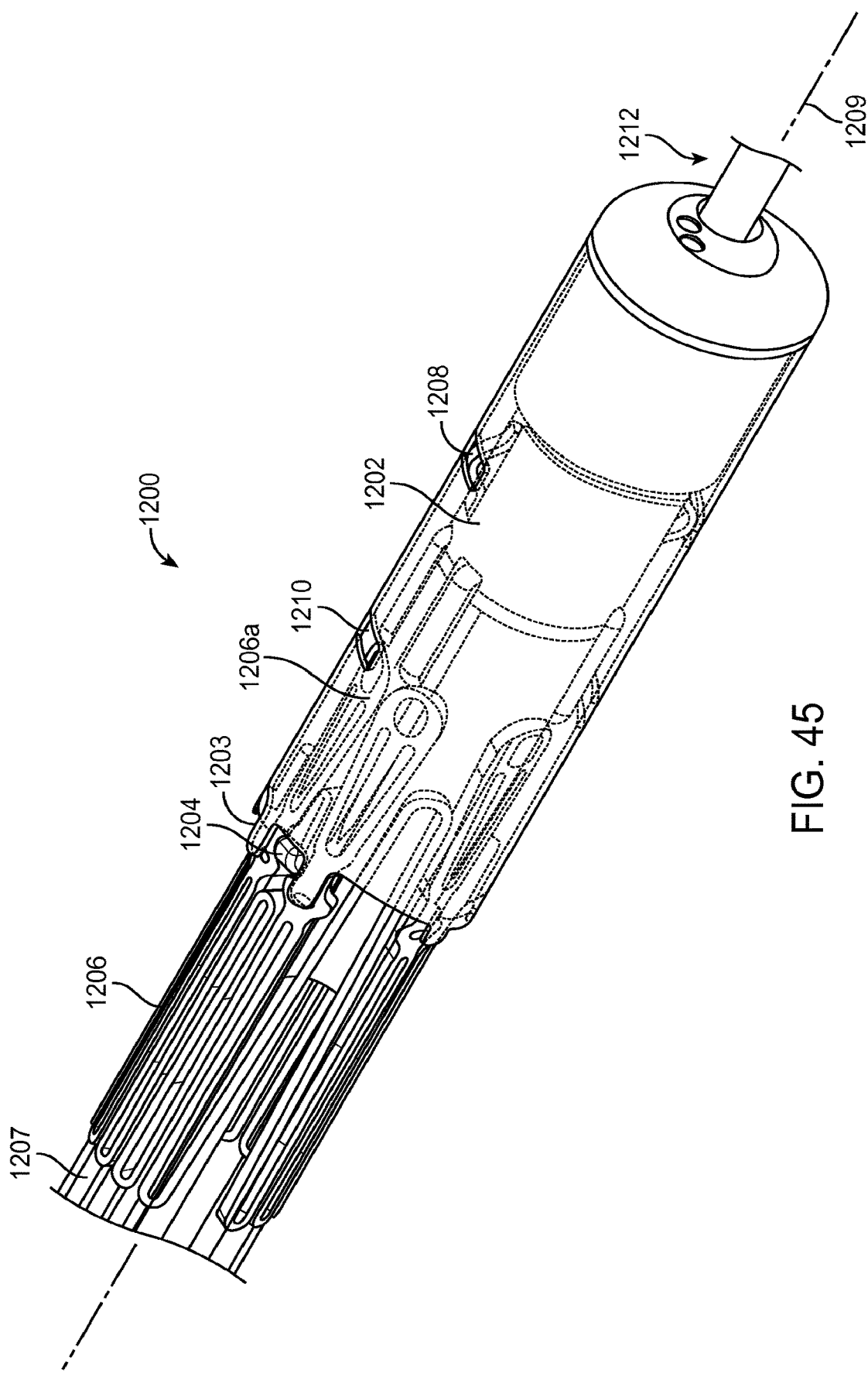
FIG. 45 shows a perspective view of an embodiment of a stent constraint system including an expandable basket and stent in a radially constrained configuration.
Figure 46:
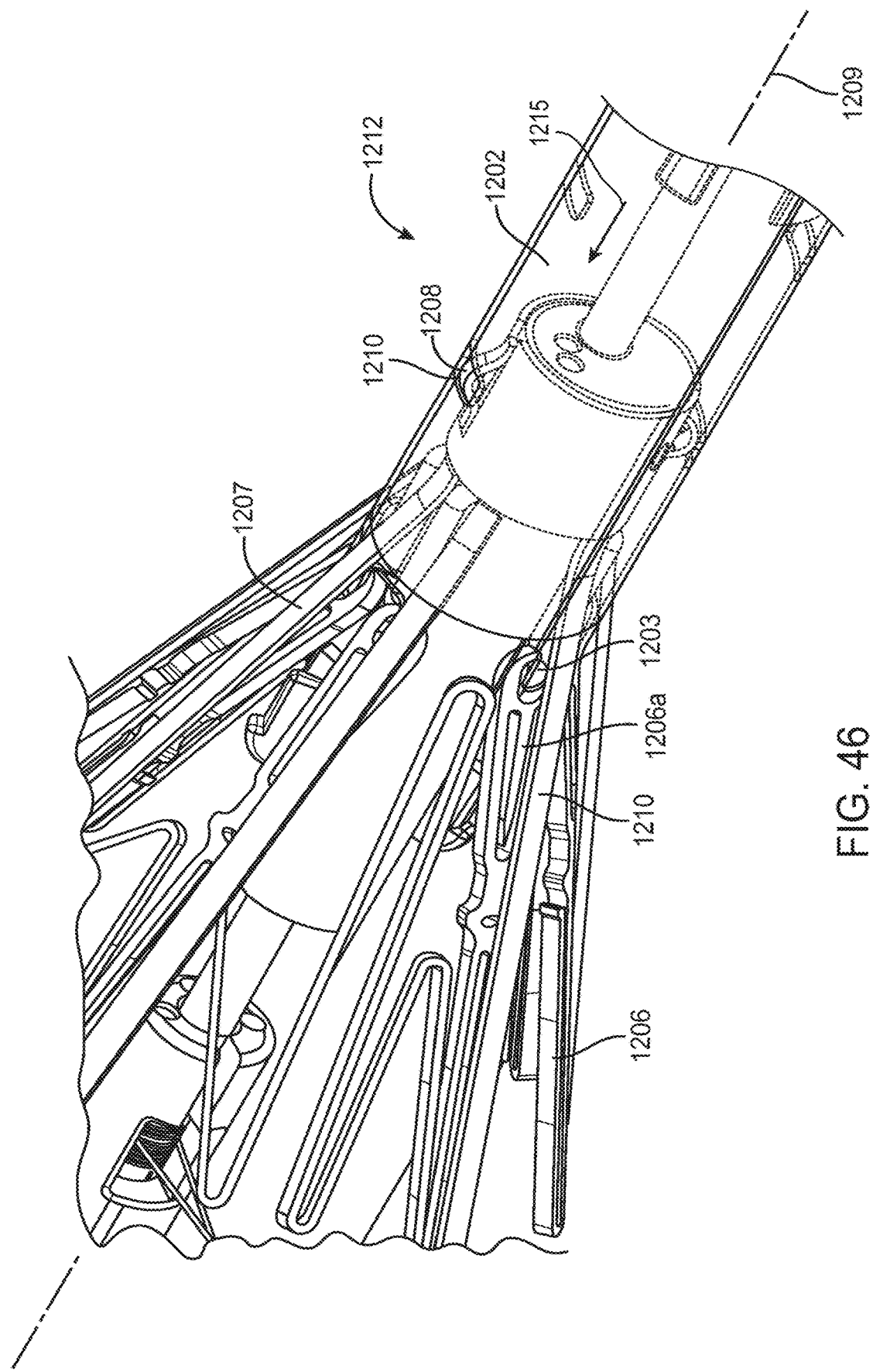
FIG. 46 is a perspective view of the constraint system of FIG. 45 with a sleeve displaced proximally relative to the stent and basket so as to partially release the stent and allow the expandable basket to radially expand.
Figure 47:
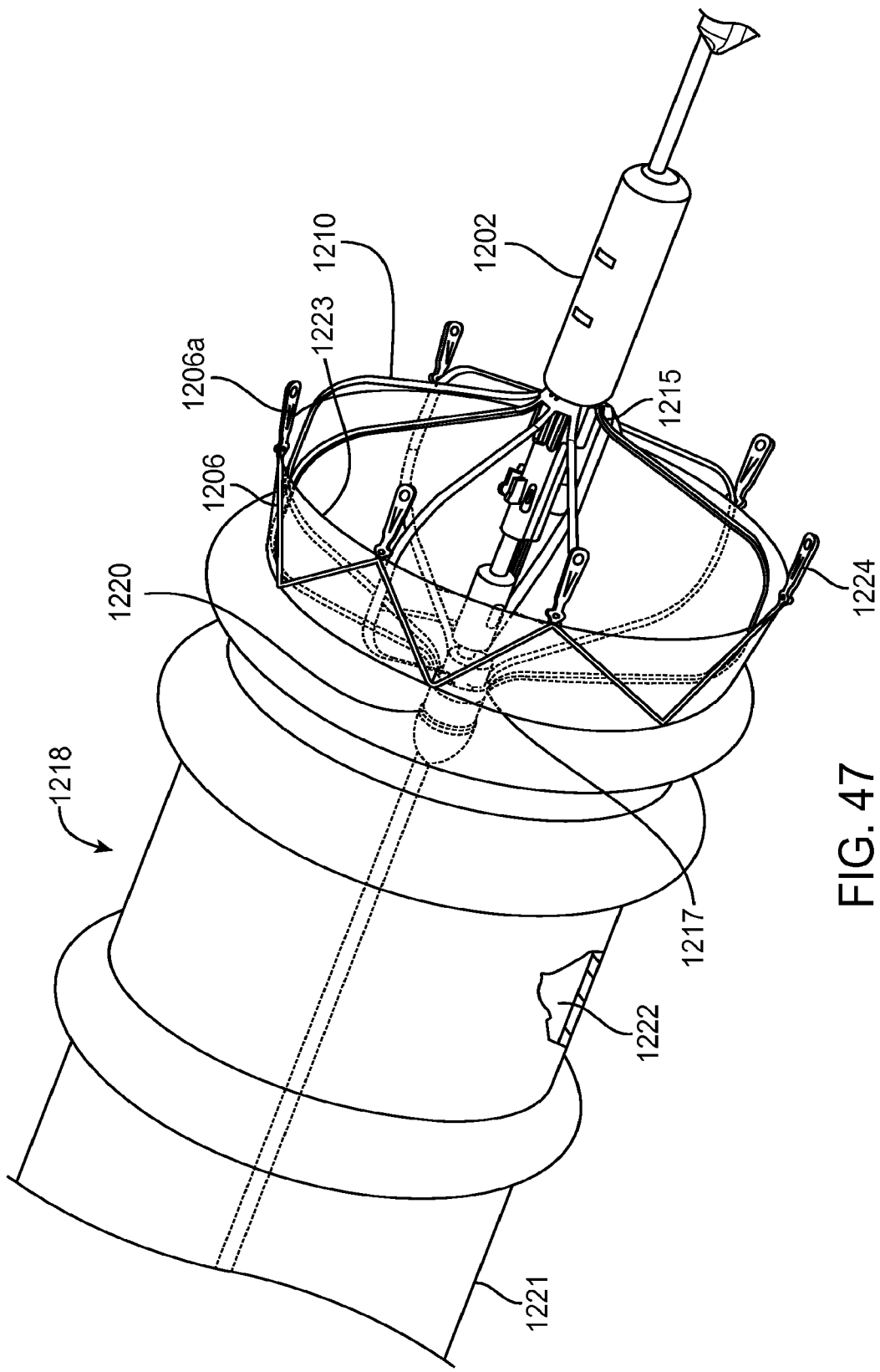
FIG. 47 is a perspective view of the constraint system of FIG. 46 wherein the stent graft previously constrained by the constraint system has been deployed and the tines of the expandable basket are applying an outward radial force against respective struts and barbs of the stent in order to more fully engage target tissue of a patient's vessel.

FIGS. 45-47 show an embodiment of a constraint system 1200 for use on a delivery catheter of a delivery system wherein a stent may be partially deployed and have barbs which are disposed on the stent mechanically pushed radially outward to aid the engagement of the barbs with the patient's vessel. FIG. 45 shows sleeve 1202 locked in a first position with lock 1208 (which in this case is constructed on one of the tines of an expandable basket 1207). Lock 1208 is shown poking through a first hole 1209 in sleeve 1202 and will be allowed to move to a second hole 1210 disposed on a different axial position of sleeve 1202. Stent 1206 and barbs 1206a are shown to be fully constrained by a crown section 1203 of sleeve 1202 disposed adjacent to support 1204.

FIG. 46 depicts a configuration when lock 1208 has been axially displaced to the second hole position 1210 in the direction of arrow 1215. In this configuration, stent 1206 has its distal portion in a flared position while the barbs 1206a are still constrained by crowns of crown section 1203. Tines 1210 of the basket 1207 are shown as deployed.

Figure 48:
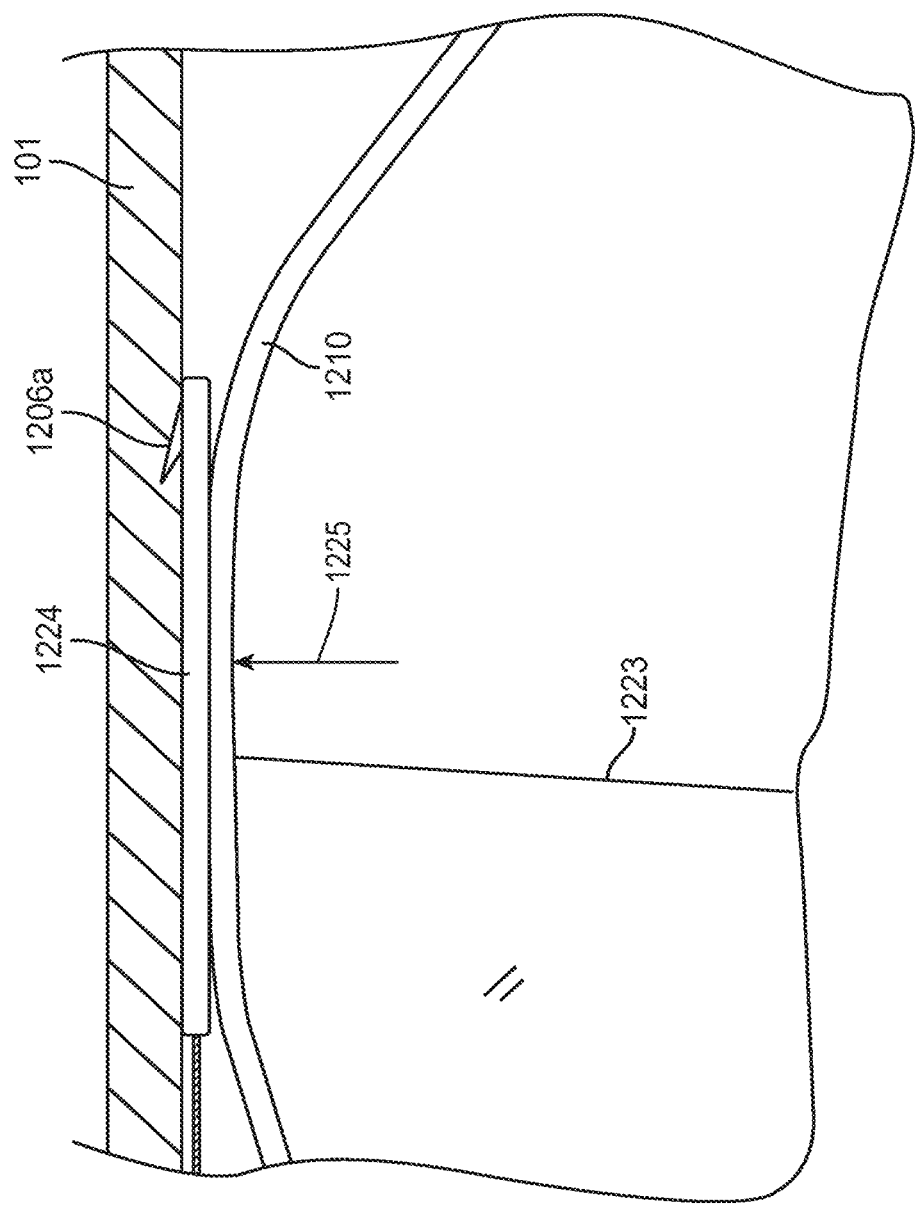
FIG. 48 is an enlarged elevation view in partial section of a tine disposed adjacent a strut and barb of a stent and applying an outward radial force against the barb towards tissue of the patient's vessel wall.

FIG. 47 shows a configuration with barbs 1206a released from all constraint and tines 1210 of the basket 1207 as deployed. It may be desirable to have first housing section 1220 to be slidably connected to sleeve 1202 so that moving sleeve 1202 towards housing section 1220 may further expand tines 1210 of the basket. By doing so, tines 1210 may push against stent struts for example in the direction of arrow 1225 as shown in FIG. 48 or the graft material (not shown) with greater radial force. This may allow some or all of barbs 1206a to better engage the luminal surface of the patient's vessel 101.

Some embodiments of a delivery system for delivering a stent graft may include a delivery catheter 501 having an elongate shaft 1212 with a proximal section and a distal section. The delivery catheter 501 may also include the releasable stent constraint system 1200 disposed on the proximal section of elongate shaft 1212 as shown in FIG. 45. The stent constraint system 1200 may include the stent constraint sleeve 1202 which may have a rigid tubular structure slidably disposed about the elongate shaft 1212. The stent constraint sleeve 1202 may be axially translatable between a distal position as shown in FIG. 45 and a proximal position as shown in FIG. 46. The stent constraint sleeve 1202 may also include a plurality of the crown sections 1203 that extend distally from the crown constraint sleeve 1202 and are circumferentially spaced from each other. The constraint system 1200 may further include the plurality of strut supports 1204 which are secured to the elongate shaft 1212 distally adjacent the stent constraint sleeve 1202. The strut supports 1204 may be circumferentially spaced from each other and extend radially outward or away from a longitudinal axis 1209 of the elongate shaft 1212.

Such a constraint system 1200 may have a constraint state wherein the stent constraint sleeve 1202 is disposed in the distal position as shown in FIG. 45 and a deployment state wherein the stent constraint sleeve 1202 is in the proximal position as shown in FIG. 46. The delivery catheter 501 may also include the expandable basket 1207 having a plurality of elongate tines 1210 which are disposed in a substantially tubular configuration, which extend axially along the elongate shaft 1212 of the delivery catheter 501 in a position distally adjacent the stent constraint sleeve 1202, and which are configured to bow radially outward upon reduction of a separation between proximal ends 1215 of the elongate tines 1210 and distal ends 1217 of the elongate tines 1210. In addition, the delivery system 501 may have a stent graft 1218 including a flexible main graft body 1221 and a self-expanding stent, such as self-expanding stent 1206. The main graft body portion 1221 may include an inner lumen 1222 configured for confining a flow of blood therethrough, a proximal end 1223 and a distal end. The self-expanding stent 1206 may have a proximal end, a distal end secured to the proximal end of the main graft body 1221, and a plurality of proximal stent crowns 1223 which include at least one barb 1206a.

For such a configuration, the stent graft 1218 may be loaded on the proximal section of the elongate shaft 1212 with the elongate shaft disposed within the inner lumen of the graft body 1222. The plurality of proximal stent crowns 1223 which include at least one barb 1206a may be disposed within and radially constrained by the stent constraint sleeve 1202 with the stent constraint sleeve 1202 in the distal position. In addition, at least one elongate tine 1210 of the expandable basket 1207 may be disposed beneath a stent crown 1223 that includes a barb 1206a, the at least one elongate tine 1210 being configured to apply outward radial force on the stent crown 1223 upon deployment of the stent 1206 and expansion of the expandable basket 1207.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although embodiments of the invention have been described in substantial detail with reference to one or more specific embodiments, those of ordinary skill in the art will recognize that changes may be made to the embodiments specifically disclosed in this application, yet these modifications and improvements are within the scope and spirit of the invention.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claim(s) that follow(s).

What is claimed is:

1. A delivery system for delivering a stent graft, comprising:
    a delivery catheter comprising an elongate shaft;
    a stent graft having a stent portion and a main graft body with an inner lumen, the stent graft being loaded on a section of the delivery catheter such that the elongate shaft is disposed within the inner lumen;
    an expandable device having an expandable portion, the expandable portion disposed on the elongate shaft within the inner lumen and configured to fully radially expand within the inner lumen to radially expand the main graft body; and
    a constraining device configured to radially constrain the stent portion in a radially constrained state while the main graft body is radially expanded, and
    wherein the expandable device is configured to be expanded prior to deployment of the stent portion of the stent graft.

2. The delivery system of claim 1, wherein the expandable device comprises an expanded basket including elongate tines, wherein the elongate tines are configured to extend substantially parallel to a portion of the elongate shaft of the delivery catheter when the elongate tines are in a contracted configuration, and wherein the elongate tines are configured to bow radially outwardly from the portion of the elongate shaft in a substantially concentric arrangement when the elongate tines are in an expanded configuration.

3. The delivery system of claim 2, wherein the elongate tines are configured to self-expand to the expanded configuration.

4. The delivery system of claim 2, wherein the elongate tines are configured to expand to the expanded configuration due to an axial compressive force applied to at least one end of the tines.

5. The delivery system of claim 1, wherein the expandable device comprises an expanding basket, the expanding basket including elongate tines that extend substantially parallel to the longitudinal axis of the portion of the elongate shaft disposed under the elongate tines when the elongate tines are in a contracted configuration.

6. The delivery system of claim 1, wherein the expandable device comprises an expanding basket, the expanding basket including elongate tines having a central portion substantially parallel to the longitudinal axis of the portion of the elongate shaft disposed under the elongate tines when the elongate tines are in an expanded configuration.

7. The delivery system of claim 1, wherein the constraining device comprises a belt.

8. The delivery system of claim 1, wherein the stent portion is secured to an end portion of the main graft body and extends eternally to the main graft body.

9. The delivery system of claim 8, wherein the end portion is a proximal end portion of the main graft body.

10. The delivery system of claim 1, wherein the stent portion comprises a proximal stent portion and a distal stent portion connected or integral with the proximal stent portion, and wherein the distal stent portion is at least partially secured to the main graft body.

11. The delivery system of claim 10, wherein the proximal stent portion includes at least one barb extending radially outward therefrom.

12. A method of centering a delivery system during deployment of a stent graft, comprising:
    providing a delivery system for delivering a stent graft, the delivery system comprising:
        a delivery catheter comprising an elongate shaft;
        a stent graft having a stent portion and a main graft body with an inner lumen, the stent graft being loaded on a section of the delivery catheter such that the elongate shaft is disposed within the inner lumen; and
        an expandable device having an expandable portion disposed on the elongate shaft within the inner lumen of the main graft body, the expandable portion configured to radially expand within the inner lumen of the main graft body while the stent portion is radially constrained to radially expand the main graft body;
    positioning the delivery catheter within a patient's vessel such that the stent graft is axially positioned at a desired state within the patient's vessel with the expandable device in a radially contracted state;
    expanding the expandable device to a radially expanded state, within the inner lumen of the main graft body, to center the elongate shaft and stent graft of the delivery system toward a longitudinal axis of the patient's vessel; and
    deploying a stent of the stent graft so as to engage an inner luminal wall of the patient's vessel, after expanding the expandable device;
    wherein said stent of the stent graft is in a constrained state when the expandable device is fully expanded within the inner lumen of the main graft body, and
    wherein the expandable device is expanded prior to deployment of the stent portion of the stent graft.

13. The method of claim 12, wherein deploying the stent comprises deploying a stent disposed at a proximal end of the stent graft disposed towards a source of blood flow in the patient's vessel.

14. The method of claim 12, wherein the expandable device comprises a basket, and wherein expanding the expandable device comprises allowing self-expanding elongate tines of the basket to self-expand to the radially expanded state.

15. The method of claim 12, wherein the expandable device comprises a basket, and wherein expanding the expandable device comprises axially compressing at least one end of elongate tines of the basket to shorten a separation of proximal ends and distal ends of the elongate tines of the basket and expand a center portion of the elongate tines to the radially expanded state.

16. The method of claim 12, wherein the expandable device comprises an inflatable structure, and wherein expanding the expandable device comprises inflating an interior volume of the inflatable structure with a biocompatible fluid to expand the inflatable structure to the radially expanded state.

17. The method of claim 12, wherein expanding the expandable device to the radially expanded state to center the elongate shaft and stent graft of the delivery system toward the longitudinal axis of the patient's vessel comprises expanding the expandable device to an outer transverse dimension which is about the same as a transverse dimension of an inner lumen of the patient's vessel at a position of the expandable device.

18. A delivery system for delivering a stent graft, comprising:
    a delivery catheter comprising an elongate shaft;
    a stent graft having a stent portion and a main graft body with an inner lumen, the stent graft being loaded on a section of the delivery catheter such that the elongate shaft is disposed within the inner lumen;

an expandable device having an expandable portion, the expandable portion disposed on the elongate shaft within the inner lumen and configured to fully radially expand within the inner lumen to radially expand the main graft body; and a constraining device configured to radially constrain the stent portion in a radially constrained state while the main graft body is radially expanded, wherein the expandable device comprises an inflatable structure including:

a collapsed deflated state; and an enlarged inflated state with a substantially cylindrical configuration including vias that extend from ports in a proximal surface of the expandable device to respective ports in a distal surface of the expandable device;

wherein the constraining device is configured to radially constrain the stent portion in a radially constrained state while the main graft body is fully radially expanded, and wherein the expandable device is configured to be expanded prior to depolyment of the stent portion of the stent graft.

19. The delivery system of claim 18, wherein the vias have a cumulative cross section that is at least about 5 percent to about 10 percent of the total cross section of the expandable device in an expanded state.

20. The delivery system of claim 18, wherein the expandable device comprises a configuration that is radially concentric with the elongate shaft in the enlarged inflated state.

* * * * *